US008512249B2

(12) United States Patent
Frinking et al.

(10) Patent No.: US 8,512,249 B2
(45) Date of Patent: Aug. 20, 2013

(54) DETECTION OF THE DETACHMENT OF IMMOBILIZED CONTRAST AGENT IN MEDICAL IMAGING APPLICATIONS

(75) Inventors: Peter Frinking, Geneva (CH); Tristan Messager, Geneva (CH); Marcel Arditi, Geneva (CH); Nicolas Rognin, Geneva (CH)

(73) Assignee: Bracco International BV, Amsterdam (NL)

( * ) Notice: Subject to any disclaimer, the term of this patent is extended or adjusted under 35 U.S.C. 154(b) by 1074 days.

(21) Appl. No.: 12/520,839

(22) PCT Filed: Dec. 21, 2007

(86) PCT No.: PCT/EP2007/064501
§ 371 (c)(1),
(2), (4) Date: Jun. 22, 2009

(87) PCT Pub. No.: WO2008/074889
PCT Pub. Date: Jun. 26, 2008

(65) Prior Publication Data
US 2009/0304593 A1    Dec. 10, 2009

(30) Foreign Application Priority Data
Dec. 21, 2006   (EP) ..................................... 06126850

(51) Int. Cl.
*A61B 5/05*   (2006.01)
*A61B 6/00*   (2006.01)
*G06K 9/00*   (2006.01)

(52) U.S. Cl.
USPC ............................ 600/458; 600/437; 382/128

(58) Field of Classification Search
USPC .................. 128/128, 129–133; 600/458, 437
See application file for complete search history.

(56) References Cited

U.S. PATENT DOCUMENTS

| 5,456,255 A | 10/1995 | Abe et al. | |
| 6,676,606 B2 * | 1/2004 | Simpson et al. | 600/458 |
| 6,740,039 B1 | 5/2004 | Rafter et al. | |
| 7,998,076 B2 * | 8/2011 | Phillips et al. | 600/458 |

(Continued)

FOREIGN PATENT DOCUMENTS

| EP | 0458745 | 11/1991 |
| EP | 0554213 | 8/1993 |

(Continued)

OTHER PUBLICATIONS

Patrick Rafter, Patrick Phillips Mani A. Vannan, "Imaging technologies and techniques", Cardiology Clinics 22 (2004), pp. 181-197.

(Continued)

*Primary Examiner* — Long V. Le
*Assistant Examiner* — Helene Bor
(74) *Attorney, Agent, or Firm* — Graybeal Jackson LLP

(57) ABSTRACT

An input image includes a plurality of input values (i.e., pixel or voxel values), each input value indicative of a response to an interrogation signal of a corresponding location of a body-part, which possibly includes a contrast agent. At least one filtered image is generated from a plurality of selected input images and includes a filtered value for each of a plurality of selected ones of the locations. Each filtered value is indicative of the contrast agent leaving the selected location and is obtained by reducing a contribution of the contrast agent that is substantially stationary at the selected location along the selected input images for a period of time equal to or shorter than a first threshold and by reducing a contribution of the contrast agent that is substantially stationary for a period of time equal to or longer than a second higher threshold.

23 Claims, 10 Drawing Sheets

(56) References Cited

U.S. PATENT DOCUMENTS

2002/0165454 A1* 11/2002 Ogasawara et al. ............ 600/443

FOREIGN PATENT DOCUMENTS

| EP | 1568323 | | 8/2005 |
|---|---|---|---|
| JP | 2002209898 | A | 7/2002 |
| JP | 2005237738 | A | 9/2005 |
| JP | 2005528949 | A | 9/2005 |
| WO | 9115244 | | 10/1991 |
| WO | 9409829 | | 5/1994 |
| WO | 9516467 | | 6/1995 |
| WO | 2004110279 | | 12/2004 |
| WO | WO2006051831 | A1 | 10/2005 |
| WO | 2006015971 | | 2/2006 |
| WO | 2006018433 | | 2/2006 |
| WO | 2007054544 | | 5/2007 |

OTHER PUBLICATIONS

Suzanne C. Kuo, Douglas A. Lauffenburger, "Relationship between Receptor/Ligand Binding Affinity and Adhesion Strength", Biophysical Journal, vol. 65. Nov. 1993, pp. 2191-2200.

Gregory E.R. Weller, Erxiong Lu, Melissa M. Csikari, Alexander L. Klibanov, David Fischer, William R. Wagner, Flordeliza S. Villanueva; "Ultrasound Imaging of Acute Cardiac Transplant Rejection With Microbubbles Targeted to Intercellular Adhesion Molecule-1" Circulation, vol. 108, Jun. 30, 2003, pp. 218-224, XP002380571.

International Search Report, based on International Application Serial No. PCT/EP2007/064501, European Patent Office, Apr. 9, 2008.

Jonathan R. Lindner, "Targeted Ultrasound Contrast Agents: Diagnostic and Therapeutic Potential", 2001 IEEE Ultrasonics Symposium Proceedings, New York, vol. 2 of 2, Oct. 7, 2001, pp. 1695-1703 (XP010584839).

Gregory M. Lanza and Samuel A. Wickline, "Targeted Ultrasound Contrast Agents for Molecular Imaging and Therapy", Progress in Cardiovascular Diseases, Philadelphia, PA, vol. 44, No. 1, Jul. 2001, pp. 13-31 (XP008034236).

Gregory M. Lanza et al., "Targeted Ultrasonic Contrast Agents for Molecular Imaging and Therapy," Progress in Cardiovascular Diseases, Jul./Aug. 2001, pp. 13-31, vol. 44, No. 1, St. Louis, MO.

* cited by examiner

DETECTION OF THE DETACHMENT OF IMMOBILIZED CONTRAST AGENT IN MEDICAL IMAGING APPLICATIONS

PRIORITY CLAIM

The present application is a national phase application filed pursuant to 35 USC §371 of International Patent Application Serial No. PCT/EP2007/064501, filed Dec. 21, 2007; which further claims the benefit of European Patent Application 06126850.4, filed Dec. 21, 2006; all of the foregoing applications are incorporated herein by reference in their entireties.

TECHNICAL FIELD

An embodiment of the present invention relates to the medical imaging field. More specifically, an embodiment of the present invention relates to contrast agent imaging applications.

BACKGROUND

Medical imaging is a well-established technique (in the field of equipments for medical applications), which allows analyzing a body-part of a patient in a substantially non-invasive manner. A specific medical imaging technique is based on the recording of an echo signal that results from the application of ultrasound waves to the body-part. This technique may advantageously be implemented with the administration of an ultrasound contrast agent (UCA) to the patient (for example, consisting of a suspension of phospholipid-stabilized gas-filled microbubbles); as the contrast agent acts as an efficient ultrasound reflector, it enhances the visualization of the vascular system within the body-part where it is present.

Target-specific contrast agents, adapted to reach a specific (biological) target and then remain immobilized thereon, have also been proposed in the last years for facilitating the detection of specific pathologies. Particularly, a target-specific contrast agent is capable of attaching to the corresponding target—such as particular tissues or receptors—by means of a specific interaction therewith; for example, the desired behavior may be achieved by incorporating a target-specific ligand in the formulation of the contrast agent (such as capable of interacting with inflammatory or tumoral tissues). Once the target-specific contrast agent has reached the target remaining immobilized thereon, its detection may allow distinguishing pathologies that would be otherwise difficult to identify.

A problem associated with the target-specific contrast agents is that only a relatively small fraction of the total amount of the administered target-specific contrast agent actually reaches the target and remains immobilized thereon. Most of the target-specific contrast agent continues to circulate, for example, until it is filtered out by the lungs and/or in the liver of the patient. The echo signal that is measured is then the result of different contributions, which are due to the immobilized (target-specific) contrast agent, to the circulating or free-flowing (target-specific) contrast agent and to surrounding tissue. Therefore, it is quite difficult to distinguish the echo signal generated by the immobilized contrast agent from the one generated by the circulating contrast agent and tissue; particularly, it is almost impossible to differentiate the low concentration of the immobilized contrast agent (often consisting of single particles thereof that reach the target individually) from the far higher concentration of the circulating contrast agent.

In the current practice, it is necessary to wait until the circulating contrast agent has completely disappeared (i.e., filtered out) before the immobilized contrast agent can be identified. However, this may require a relatively long time (up to tens of minutes).

A solution for facilitating the detection of the immobilized contrast agent is disclosed in the International patent application No. PCT/EP2006/068305 filed on 9 Nov. 2006 (the entire disclosure of which is herein incorporated by reference). The proposed solution exploits the difference in flow dynamics between the immobilized contrast agent and the circulating contrast agent. Particularly, the echo signal is filtered so as to remove (possibly high-) intensity peaks of short durations caused by the (fast) passage of the circulating contrast agent; the durations of the intensity peaks are shorter than a predefined filtering window. The desired result is achieved by applying a modified version of the Minimum Intensity Projection (Min_IP) algorithm. This allows detecting the immobilized contrast agent with an acceptable degree of accuracy at an early instant after the administration of the target-specific contrast agent to the patient (for example, in the first 2-5 minutes).

Nevertheless, the detection of the target-specific contrast agent that is actually immobilized (i.e., it remains attached to the desired target substantially permanently) is hindered by several disturbing factors.

For example, a problem may be caused by a non-specific interaction of the target-specific contrast agent with a passive target. In this case, the target-specific contrast agent detaches after having been immobilized temporarily, because the non-specific interaction is weaker than the specific-interaction with the intended (active) target; typically, this happens when the passive target includes a receptor similar to the one of the active target, or when the target-specific contrast agent has lost its specificity in the patient (such as under the action of his/her immune system). Anyway, this temporarily-immobilized contrast agent—while it is attached to the passive target—is completely indistinguishable from the permanently-immobilized contrast agent. Therefore, if the body-part is analyzed at an early instant after the administration of the target-specific contrast agent to the patient, any temporarily-immobilized contrast agent leads to an incorrect identification and localization of the desired target (false positives).

Moreover, the above-described solution is unable to discriminate the permanently-immobilized contrast agent from the circulating contrast agent that moves very slowly (such as at the micro-vascular level). Particularly, when the slowly-moving contrast agent remains around the same locations for a period of time longer than the filtering window of the modified Min_IP algorithm, it appears as immobilized at these instants; indeed, the intensity peaks of the echo signal caused by this apparently-immobilized contrast agent are too broad to be removed by the modified Min_IP algorithm.

All of the above may adversely affect the spatial delineation and the quantification of the permanently-immobilized contrast agent, thereby hindering the correct detection of the pathologies of interest.

SUMMARY

In its general terms, an embodiment of the present invention is based on the idea of detecting the contrast agent that detaches after being substantially stationary (for example, because it is temporality-immobilized or apparently-immobilized).

More specifically, an embodiment of the invention is a method for imaging a body-part that is perfused with a contrast agent. The method includes the step of providing a sequence of input images (for example, acquired with an ultrasound scanner); the input images offer a digital representation over time of the body-part. Each input image includes a plurality of input values (i.e., pixel or voxel values); each input value is indicative of a response to an interrogation signal (such as an echo signal for ultrasound waves) of a corresponding location of the body-part, which possibly includes the contrast agent. The method further includes the step of generating at least one filtered image from a plurality of selected ones of the input images (such as all of them or a subset thereof). Each filtered image includes a filtered value for each of a plurality of selected ones of the locations (for example, in a region of interest, or ROI). The filtered value is obtained by reducing, where present, a contribution of the contrast agent that is substantially stationary at the selected location along the selected input images for a period of time equal to or shorter than a first non-zero threshold. According to an embodiment of the invention, this operation of reducing the contribution of any circulating contrast agent may be omitted when this contribution is not included in the input images (e.g., because the contribution has been previously removed or because the input images were acquired after disappearance of the circulating contrast agent). In addition to the above, the filtered value is obtained by also reducing a contribution of the contrast agent that is substantially stationary at the selected location along the selected input images for a period of time equal to or longer than a second threshold higher than the first threshold. The filtered value of each selected location is thus indicative of the contrast agent that leaves the selected location after being substantially stationary at the selected location for a period of time, which is comprised between the first threshold and the second threshold (e.g., because the contrast agent detaches from the location after having been immobilized thereon for a certain period).

In an embodiment, a target-specific contrast agent is used.

In a specific implementation, the selected input images are pre-processed to reduce a contribution of the circulating contrast agent; each filtered value is then calculated by cumulating a variation value, which is indicative of the variation of a comparison value (based on a corresponding set of input values from a comparison set of the selected input images) with respect to a reference value (consisting of the preceding input value).

In a different implementation, the same result may be achieved by combining the two operations in a single step—with each variation value that is now indicative of the variation of the comparison value with respect to a reference value, being based on the lowest response (i.e., the minimum) in a set of preceding input values.

Typically, a further sequence of filtered images is generated (with each filtered value that is obtained by cumulating the variation value with the preceding filtered value).

The proposed embodiment may be particularly advantageous when each filtered image is displayed in substantial synchrony with an acquisition instant of a specific selected input image corresponding thereto (i.e., with a short delay but without waiting for the completion of the acquisition process), thus providing a real-time display of the filtered images.

In an embodiment of the invention, the comparison set of selected input images consists of the specific selected input image only (with the comparison value that is set to the corresponding input value directly).

Alternatively, the comparison set of selected input images consists of the specific selected input image and one or more selected input images preceding the specific selected input image in the sequence.

In the latter case, it is also possible to temporally sub-sample the comparison set of selected input images (for example, when a frame rate is extremely high).

Typically, the comparison value is set to the input value of the comparison set that is indicative of the highest response (i.e., the echo signal) at the selected location.

For example, when the input values increase with the responses at the corresponding locations, this result is achieved by setting the comparison value to the maximum input value of the comparison set.

In a proposed implementation, the variation value is set to the absolute value of the difference between the comparison value and the reference value.

In an embodiment, the variation value is set to a delta value, which is indicative of the subtraction of the comparison value from the reference value at the selected location (when the response—i.e., the echo signal—decreases from the reference value to the comparison value), or to a null value otherwise.

For example, when the input values increase with the responses at the corresponding locations, the variation value is set to the reference value minus the comparison value (when the comparison value is lower than the reference value), or to zero otherwise.

Typically, a contribution of tissue in the selected input images has been substantially removed, or at least reduced (for example, by acquiring them with a contrast-specific imaging mode).

A way to further improve the solution is to subtract a background image (for example, taken before the arrival of the contrast agent in the body-part) from the selected input images.

In an implementation, the selected input images are spatially sub-sampled according to an estimated resolution thereof (for example, based on the size of speckle grains that typically occur in ultrasound imaging).

As a further improvement, it is possible to compensate a relative motion of each selected input image (with respect to a reference image).

Moreover, the selected input images may also be linearized (so as to make their input values substantially proportional to a concentration of the contrast agent at the corresponding locations).

The filtered images may be overlaid onto the input images—for example, by overriding the representation of the permanently-immobilized contrast agent with the representation of the temporarily/apparently-immobilized contrast agent (preferably over a background representing the body-part under analysis).

In this case, it may be advised to use different visual coding for the filtered values and the input values (such as with the temporarily/apparently-immobilized contrast agent represented in color and the other information represented in gray).

Another embodiment of the present invention proposes a computer program for performing the method.

A further embodiment of the present invention proposes a corresponding system for implementing the method illustrated above.

BRIEF DESCRIPTION OF THE DRAWINGS

Features and advantages of one or more embodiments will be best understood with reference to the following detailed description, given purely by way of a non-restrictive indication, to be read in conjunction with the accompanying drawings, in which.

DETAILED DESCRIPTION

Figure 1:
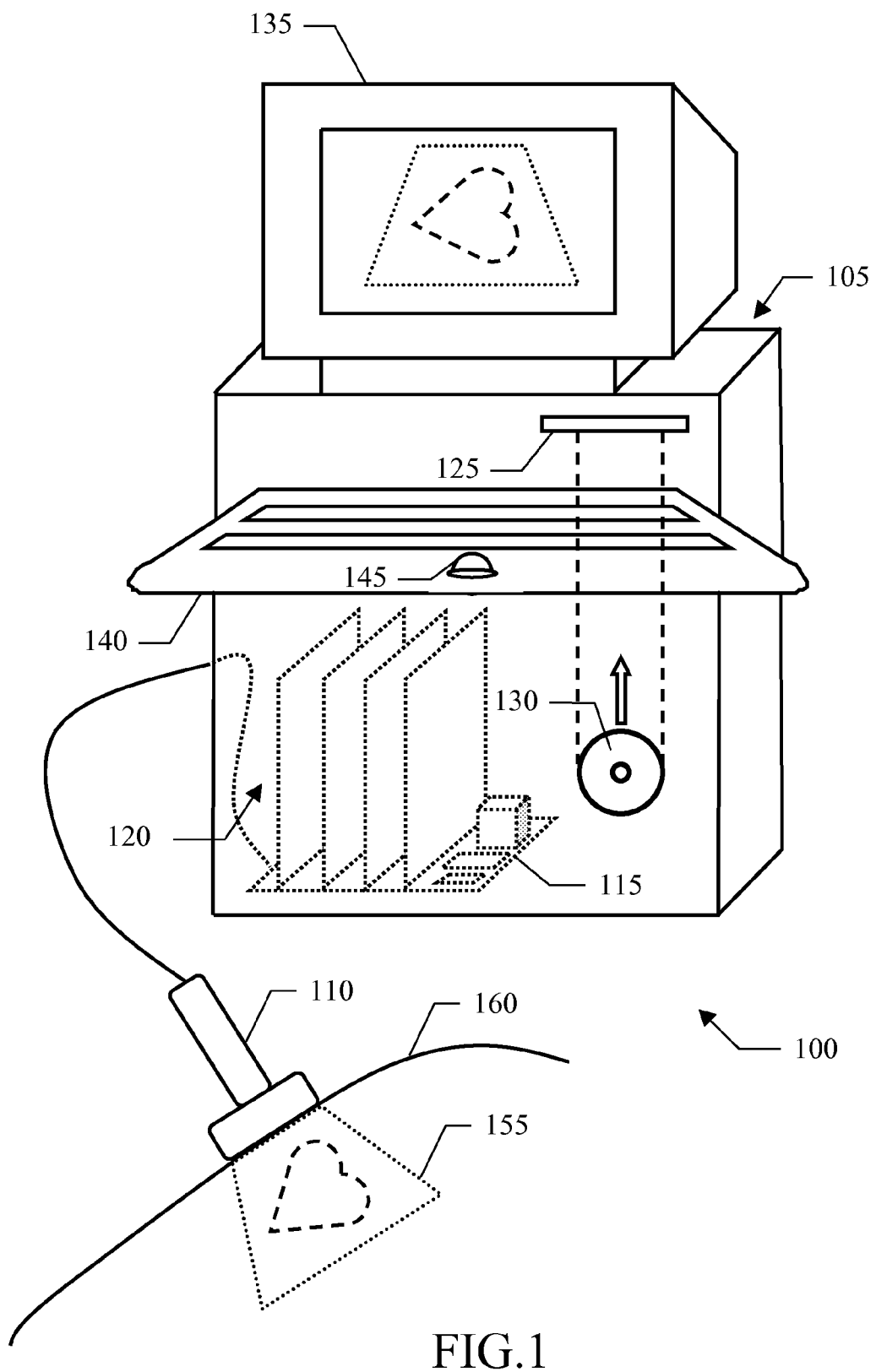
FIG. 1 is a pictorial representation of an ultrasound scanner in which the solution according to an embodiment of the invention is applicable.

With reference in particular to FIG. 1, an embodiment of a medical imaging system consisting of an ultrasound scanner 100 is illustrated. The ultrasound scanner 100 includes a central unit 105 and a hand-held transmit-receive imaging probe 110 (for example, of the array type). The imaging probe 110 transmits ultrasound waves consisting of a sequence of pulses (for example, having a center frequency between 1 and 50 MHz), and receives a (raw) radio-frequency (RF) echo signal resulting from the reflection of the ultrasound pulses; for this purpose, the imaging probe 110 is provided with a transmit/receive multiplexer, which allows using the imaging probe 110 in the above-mentioned pulse-echo mode.

The central unit 105 houses a motherboard 115, on which the electronic circuits controlling operation of the ultrasound scanner 100 (such as a microprocessor, a working memory and a hard-disk drive) are mounted. Moreover, one or more daughter boards (denoted as a whole with 120) are plugged on the motherboard 115; the daughter boards 120 provide the electronic circuits for driving the imaging probe 110 and for processing the received echo signal. The ultrasound scanner 100 can also be equipped with a drive 125 for reading removable disks 130 (such as floppy-disks). A monitor 135 displays images relating to the analysis in progress. Operation of the ultrasound scanner 100 is controlled by means of a keyboard 140, which is connected to the central unit 105 in a conventional manner; the keyboard 140 may be provided with a trackball 145 that is used to manipulate the position of a pointer (not shown in the figure) on a screen of the monitor 135.

The above-described ultrasound scanner 100 is used to analyze a body-part 155 of a patient 160. For this purpose, a contrast agent (capable of enhancing ultrasound images) is administered to the patient.

The contrast agent can be administered orally (for example, for imaging the gastrointestinal tract), via a nebulizer into the airways (for imaging the lungs), or by injection. Administration by injection includes, for instance, intravenous, intra-arterial, intralymphatic, subcutaneous, intramuscular, intradermal, intraperitoneal, interstitial, intrathecal or intratumoral administration. The contrast agent may be administered intravenously, either as a continuous infusion (typically by means of a pump) or as a bolus (typically by hand with a syringe). The contrast agent circulates within the patient, so as to be received by the body-part 155; for example, the contrast agent may move along the gastrointestinal tract (in case of oral administration), or within the vascular system (in case of intravenous administration, wherein the body-part 155 is perfused with said contrast agent). The contrast agent may be administered to the patient before and/or during the imaging of the body-part 155.

Suitable contrast agents for ultrasound imaging include suspensions of gas bubbles in a liquid carrier; typically, the gas bubbles have diameters on the order of 0.1-5 μm, so as to allow them to pass through the capillaries of the patient. The gas bubbles are generally stabilized by entraining or encapsulating the gas or a precursor thereof into a variety of systems, including emulsifiers, oils, thickeners, sugars, proteins or polymers; stabilized gas bubbles are referred to as gas-filled microvesicles. The microvesicles include gas bubbles dispersed in an aqueous medium and bound at the gas/liquid interface by a very thin envelope involving a surfactant, i.e., an amphiphilic material (also known as microbubbles). Alternatively, the microvesicles include suspensions in which the gas bubbles are surrounded by a solid material envelope formed of lipids or of natural or synthetic polymers (also known as microballoons or microcapsules). Another kind of contrast agent includes suspensions of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial ultrasound contrast agent comprising gas-filled microvesicles is SonoVue® by Bracco International BV.

The contrast agent may be a target-specific contrast agent. The target-specific contrast agent is substantially free to circulate within the patient; however, the target-specific contrast agent is also capable of being immobilized on a selected (biological) target, so as to remain in a substantially fixed position for the whole duration of an analysis process (or at least a large portion thereof).

For this purpose, the target-specific contrast agent is formulated in such a way as to bind selectively to the desired target by means of a specific interaction therewith. For example, this behavior may be achieved by incorporating a target-specific ligand capable of selectively binding (such as through biochemical affinity and/or electrostatic interaction) to a desired tissue or receptor. Examples of target-specific ligands (which may be inserted into a membrane of the microbubbles) are monoclonal antibodies, peptides, or polysaccharides. The term tissue includes (within its meaning) individual cells as well as aggregates of cells, such as membranes or organs. The term refers to either normal (healthy) or abnormal (pathological) cells or aggregates of cells. Examples of tissue are myocardial tissue (including myocardial cells and cardiomyocytes), membranous tissue (such as endothelium and epithelium), and connective tissue; examples of pathological tissue are infarcted heart tissue, blood clots, atherosclerotic plaques, inflammatory tissue and tumoral tissue. The receptors include any molecular structure located on the tissue (for example, within the cells or on their surfaces), which is capable to selectively bind to a specific substance. Exemplary receptors are glycoprotein GPIIbIIIa or fibrin (for example, located in blood clots or thrombi), P-Selectin (for example, located on activated endothelium of inflamed tissue) or KDR (for example, located in tumoral tissue). Examples of suitable target-specific contrast agents and of target-specific ligands are described in "G. M. Lanza and S. A. Wickline, Targeted Ultrasonic Contrast Agents for Molecular Imaging and Therapy, Progress in Cardiovascular Diseases, 44(1), 2001, 13-31", and in WO-A-2006018433 (the entire disclosures of which are herein incorporated by reference).

During the analysis process, the imaging probe 110 is typically placed in contact with the skin of the patient 160 in the area of the body-part 155. A series of ultrasound pulses with low acoustic energy (such as with a mechanical index MI=0.01-0.1) is applied to the body-part 155, so as to involve a negligible destruction of the contrast agent (such as less than 10%, and, for example, less than 5% of its local concentration between successive ultrasound pulses). The echo signal that is recorded in response to the ultrasound pulses over time provides a representation of the evolution of the body-part 155 during the analysis process (either while the patient 160 undergoes the administration of the contrast agent or later on). The echo signal is then converted into a sequence of digital images (or frames) in standard Brightness mode (B-mode), which images represent the body-part 155 at corresponding successive acquisition instants (for example, with a sampling rate of 10-30 images per second). Each image is defined by a bitmap consisting of a matrix (for example, with M=512 rows and N=512 columns) of values for respective visualizing elements, i.e., basic picture elements (pixels) or basic volume elements (voxels); each pixel (or voxel) corresponds to a location, which is formed by a basic portion of the body-part 155. Typically, the pixel value consists of a gray-scale level (for example, coded on 8 bits) defining the brightness of the pixel; the pixel value increases from 0 (black) to 255 (white) as a function of the intensity of the corresponding echo signal.

The echo signal and then the corresponding images generally result from the superimposition of different contributions, which are generated by the target-specific contrast agent that is still circulating, by the target-specific contrast agent that is immobilized on the target, and by surrounding tissue.

The ultrasound scanner 100 may operate in a contrast-specific imaging mode so as to substantially remove, or at least reduce, the dominant (linear) contribution of tissue in the echo signal, with respect to the (non-linear) contribution of the (circulating and immobilized) target-specific contrast agent; examples of contrast-specific imaging modes include harmonic imaging (HI), pulse inversion (PI), power modulation (PM) and contrast pulse sequencing (CPS) techniques, as described, for example, in "Rafter et al., Imaging technologies and techniques, Cardiology Clinics 22 (2004), pp. 181-197" (the entire disclosure of which is herewith incorporated by reference).

Moreover, the images may be acquired at a time point substantially delayed with respect to the administration of the target-specific contrast agent (for example, 10 minutes after its injection); in this way, the circulating contrast agent has disappeared (i.e., filtered out by the lungs and/or in the liver of the patient), so that it does not appear in the images any longer. The images may be pre-processed to substantially remove, or at least reduce, the contribution of the circulating contrast agent; for example, this result may be achieved by applying the modified Min_IP algorithm described in the above-mentioned International patent application No. PCT/EP2006/068305. In this case, the analysis process may start before or immediately after the administration of the target-specific contrast agent (without the need to wait for the complete disappearance of the circulating contrast agent).

Briefly, for this purpose each pixel value is updated by replacing it with the minimum in a filtering set including the pixel value itself and the corresponding pixel value in one or more preceding images. More specifically, the updated pixel value is obtained by applying the following formula:

$$IP(x,y,k)=\text{MIN}[VP(x,y,k) \ldots VP(x,y,k-n)] \text{ with } n \geq 1,$$

where $VP(x,y,k-i)$ is the (original) pixel value identified by the spatial coordinates x,y (row and column number, respectively) in the image taken at the instant k and in the preceding images taken from the instant k−1 back to the instant k−n, MIN{ } is a function determining the minimum between its arguments, and $IP(x,y,k)$ is the (updated) pixel value at the same instant k. The number n specifies a filtering length indicating the number of pixel values in the filtering set (i.e., the number of images) that are taken into account for calculating the desired minimum. The filtering length n corresponds to a time window (given by the product of the filtering length n by the inverse of the imaging frame rate), which defines the degree of temporal low-pass filtering applied by the modified Min_IP algorithm. Indeed, the modified Min_IP algorithm is able to remove any peak of the pixel values over time having a width smaller than the extent of the filtering window. In this way, the target-specific contrast agent is considered immobilized only when it remains at the same location for a period of time longer than the filtering window.

A solution according to an embodiment of the present invention, as described in detail in the following, is based on the idea of detecting the contrast agent that leaves any location after having been substantially stationary in it (such as for a period of time longer than the filtering window of the modified Min_IP algorithm).

A possible application of the proposed solution consists of the detection of the target-specific contrast agent that detaches after being immobilized temporarily.

Particularly, this is due to a non-specific interaction of the target-specific contrast agent with a passive target consisting of any other biological elements (i.e., tissues or receptors) different from the actual (active) target of the target-specific contrast agent. For example, the target-specific contrast agent may attach to a receptor that is similar to the active target (such as including a component interacting which the target-specific contrast agent). As another example, the target-specific contrast agent may be modified by the patient's immune system (such as when it is recognized as a non-self component of the blood, thus being opsonized by blood proteins and then phagocytosed by monocytes or macrophage); in this case, the modified target-specific contrast agent may loose its specificity or it may acquire a weaker specificity with other biological elements different from the active target. In any case, it is possible to remove the contribution of the temporarily-immobilized contrast agent from the result of the detection of the immobilized contrast agent (so as to leave the contribution of the permanently-immobilized contrast agent only). This allows avoiding any false positives caused by the incorrect identification and localization of the target (due to the temporarily-immobilized contrast agent).

Moreover, the target-specific contrast agent may also be temporarily immobilized at locations having a reduced specific interaction with the target-specific contrast agent. For example, this may be due to a low concentration of the receptors for the target-specific contrast agent. In this way, the detection of the detached contrast agent (and then of the temporarily-immobilized contrast agent) allows distinguishing pathologies at their early stage of development; moreover, the same information may be used to monitor the evolutions of pathologies already diagnosed (for example, to verify the response of the patient to a corresponding treatment).

The same solution also allows detecting the target-specific contrast agent that moves very slowly—as soon as it leaves any location where it was stationary for a period of time long enough to have it appear as immobilized (such as longer than the filtering window of the modified Min_IP algorithm). As above, the contribution of the apparently-immobilized contrast agent can be removed from the result of the detection of the immobilized contrast agent (so as to leave the contribution of the permanently-immobilized contrast agent only). This facilitates the identification and localization of the desired target, especially at the micro-vascular level.

In an embodiment of the present invention, the desired result is achieved by exploiting the persistence of the temporarily-immobilized contrast agent and the apparently-immobilized contrast agent, which is different compared to the persistence of the permanently-immobilized contrast agent. Indeed, the attachment of the permanently-immobilized contrast agent to the corresponding active target is highly persistent (the target-specific contrast agent being expressly designed for this purpose). Conversely, the persistence of the temporarily-immobilized contrast agent and the apparently-immobilized contrast agent is substantially lower. Particularly, the persistence of the temporarily-immobilized contrast agent depends on the strength of the non-specific interaction between the target-specific contrast agent and the relevant passive target (as described in "S. C. Kuo et al., Relationship between Receptor/Ligand Binding Affinity and Adhesion Strength, Biophysical Journal, 65, 1993, pp. 2191-2200", the entire disclosure of which is herewith incorporated by reference), or on the available concentration of the receptors for the target-specific contrast agent at the location. On the other hand, the persistence of the apparently-immobilized contrast agent depends on the flow velocity of the slowly-moving contrast agent.

Therefore, the echo signal originating from the permanently-immobilized contrast agent is represented in the sequence of images by corresponding pixel values (for the same location) that exhibit a high stability (from one instant to the other)—i.e., the pixel values remain substantially constant over time; conversely, the echo signal originating from the temporarily-immobilized contrast agent and the apparently-immobilized contrast agent is represented by corresponding pixel values that exhibit a low stability—i.e., the pixel values substantially decrease over time. The images are then processed so as to substantially suppress (or at least attenuate) the pixel values showing a high level of persistence (at the same time preserving the pixel values showing a low level of persistence).

For this purpose, in an embodiment of the present invention, the difference between each pixel value and the corresponding pixel value in the preceding image is calculated and accumulated. More formally, this result is achieved by applying the following proposed cumulative difference algorithm:

$$OP(x,y,k)=OP(x,y,k-1)+ABS[IP(x,y,k-1)-IP(x,y,k)],$$

where $IP(x,y,k)$ and $IP(x,y,k-1)$ are the (input) values of the pixel in the image taken at the instant k and in the preceding image taken at the instant k−1, respectively, ABS{ } is a function determining the absolute value of its argument, and $OP(x,y,k)$ and $OP(x,y,k-1)$ are the (output) value of the pixel at the same instant k and at the preceding instant k−1, respectively. In other words, the cumulative difference algorithm makes persistent any variation in consecutive pixel values (i.e., in the concentration of the contrast agent at the corresponding location over time).

Figure 2B:
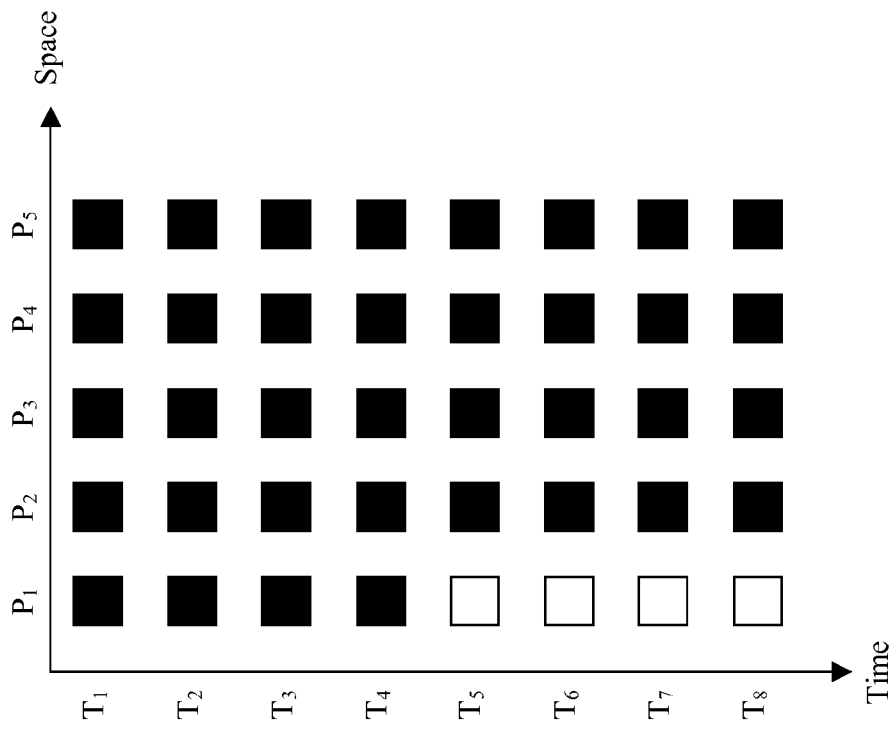
FIGS. 2a-2b are a schematic representation of an exemplary application of the solution according to an embodiment of the invention.
Figure 2A:
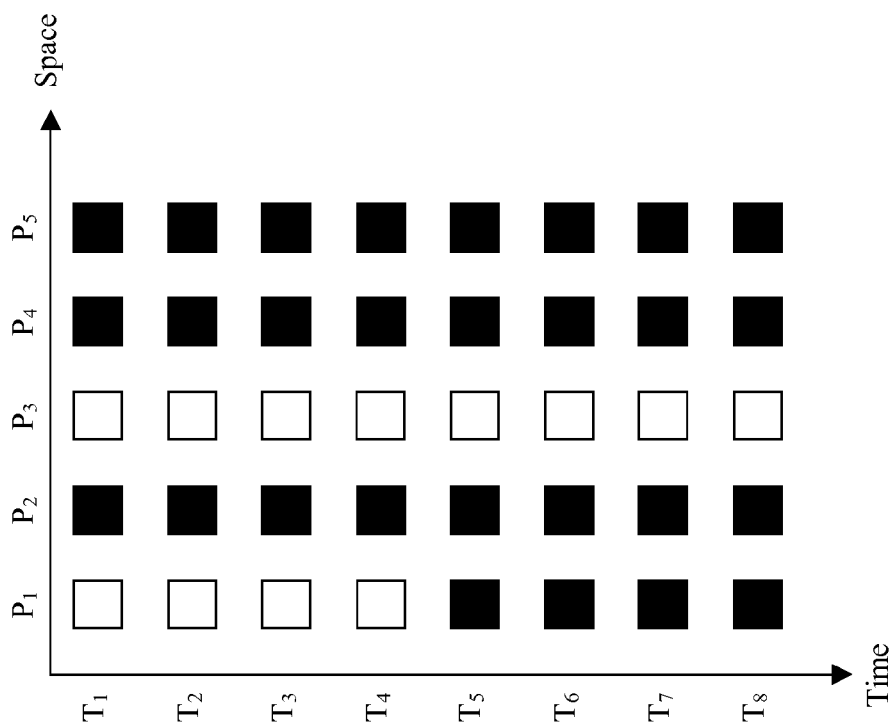

An example of application of this cumulative difference algorithm is represented schematically in FIGS. 2a-2b. Particularly, FIG. 2a shows a portion (consisting of 5 pixels $P_1$-$P_5$) of exemplary images taken at consecutive instants ($T_1$-$T_8$)—with the contribution of tissue and the contribution of the circulating contrast agent that have been completely suppressed. For the sake of simplicity, each pixel $P_1$-$P_5$ is represented as completely black in the absence of any (permanently, temporarily or apparently) immobilized contrast agent and completely white when the immobilized contrast agent is detected.

As shown in the figure, at the beginning (instant $T_1$) the pixel $P_1$ and the pixel $P_3$ are white to indicate the presence of an immobilized particle of contrast agent (such as a microbubble) at each corresponding location, while the other pixels ($P_2$, $P_4$, $P_5$) are black (since no immobilized contrast agent is present). During the instants $T_2$-$T_4$, the immobilized particles of contrast agent remain at the pixels $P_1$ and $P_3$. At the instant $T_5$, the particle of contrast agent at the pixel $P_1$ suddenly detaches and then disappears (since it is filtered out by the application of the modified Min_IP algorithm that removes the contribution of the circulating contrast agent), as shown by the pixel $P_1$ that becomes black; on the contrary, the other immobilized particle of contrast agent remains at the pixel $P_5$ for the next instants ($T_5$-$T_8$).

The application of the proposed cumulative difference algorithm to the example described above generates a corresponding image that is shown in FIG. 2b. Particularly, every pixel $P_1$-$P_5$ that does not change between consecutive images will remain black; conversely, when a pixel $P_1$-$P_5$ changes (from white to black or vice-versa) between consecutive images it becomes white and then maintains this value. As a result, the immobilized particle of contrast agents at the pixel $P_1$ (instants $T_1$-$T_4$) and at the pixel $P_3$ (instants $T_1$-$T_8$) disappear; on the contrary, the detachment of the particle of contrast agent at the pixel $P_1$ at the instant $T_5$ is detected and preserved (instants $T_5$-$T_8$).

In this way, the detachment of the immobilized contrast agent may be detected in real-time (while the images are acquired). Particularly, the detachment is revealed as soon as the target-specific contrast agent leaves its target. Therefore, the results of the analysis may be available at an early time point after the administration of the target-specific contrast agent (without the need of waiting for the completion of its wash-out phase).

Although quite effective in detecting the detached contrast agent, the above-described cumulative difference algorithm might suffer some problems when the analysis process starts before some particles of the target-specific contrast agent are immobilized; typically, this happens when the target-specific contrast agent is immobilized substantially late—such as 5-10 minutes after its administration (during late phase opacification).

Figure 3C:
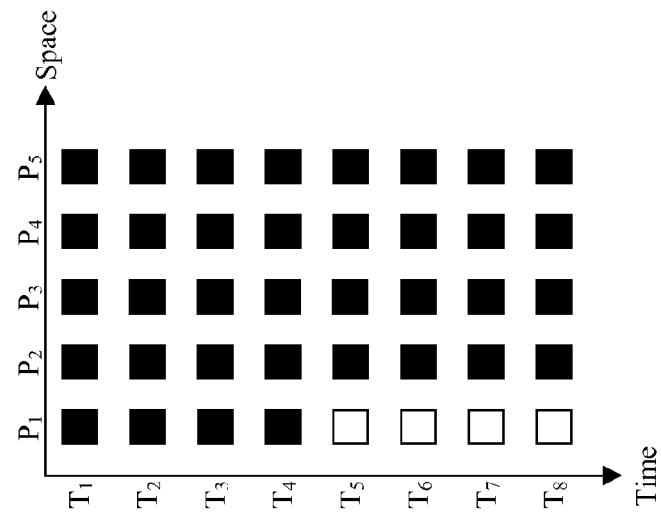
FIGS. 3a-3c are a schematic representation of an exemplary application of the solution according to a different embodiment of the invention.
Figure 3B:
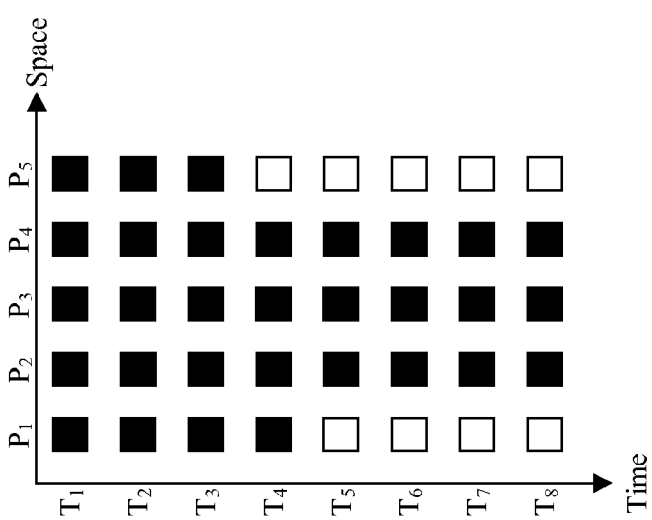
Figure 3A:
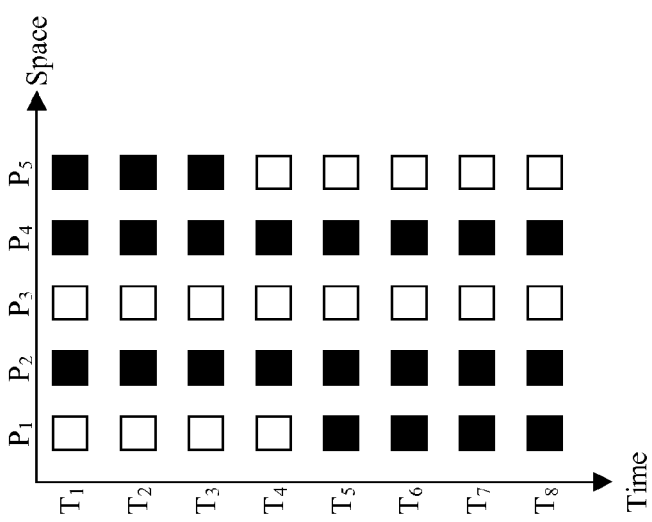

For example, the application of the cumulative difference algorithm to such an exemplary condition is represented schematically in FIGS. 3a-3c.

Particularly, in FIG. 3a the same scenario described in FIG. 2a is repeated for the pixels $P_1$-$P_4$. However, a further particle of contrast agent is immobilized at the pixel $P_5$ at the instant $T_4$, and it remains there for the next instants ($T_5$-$T_8$). The application of the cumulative difference algorithm to this example generates a corresponding image that is shown in FIG. 3b. As in the preceding case, the immobilized particle of contrast agents at the pixel $P_1$ (instants $T_1$-$T_4$) and at the pixel $P_3$ (instants $T_1$-$T_8$) disappear, while the detached particle of contrast agent at the pixel $P_1$ is detected and preserved (instants $T_5$-$T_8$). However, when the pixel $P_5$ changes (from black to white) at the instant $T_4$ in FIG. 3a, it becomes white and then maintains this value; therefore, the attachment of the particle of contrast agent at the pixel $P_5$ at the instant $T_4$ is likewise detected and remains visible during the next instants $T_5$-$T_8$.

In other words, the cumulative difference algorithm in the form provided above confuses the detached contrast agent with the contrast agent that immobilizes later on (even if it remains so); this is due to the fact that the cumulative difference algorithm makes persistent any variation of consecutive pixel values in both directions (i.e., when they either decrease or increase).

However, the above-mentioned problem may be solved by modifying the cumulative difference algorithm according to the following formula:

$$OP(x,y,k)=OP(x,y,k-1)+\text{MAX}[0,IP(x,y,k-1)-IP(x,y,k)],$$

where MAX{ } is a function determining the maximum between its arguments. In other words, the modified cumulative difference algorithm now makes persistent the decrease in consecutive pixel values only (indicative of a reduction of the concentration of the contrast agent at the corresponding location over time).

The application of the modified cumulative difference algorithm to the same scenario of FIG. 3a generates a corresponding image that is shown in FIG. 3c. As can be seen, the pixels $P_2$-$P_5$ remain always black (instants $T_1$-$T_8$), since their values are stationary or increase; as above, the pixel $P_1$ becomes white at the instant $T_5$ and then remains so (since its value decreases). Therefore, the contribution of the immobilized contrast agent completely disappears (even if it is immobilized late).

A further problem may be caused by the immobilized contrast agent that transiently disappears in the images (even if it disappears for a very short time, down to a single image); typically, this is due to noise in the images or to their misalignment.

Figure 4C:
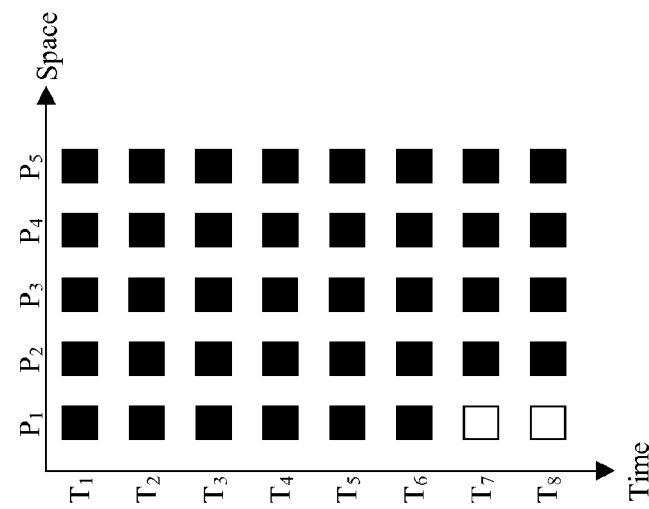
FIGS. 4a-4c are a schematic representation of an exemplary application of the solution according to a further embodiment of the invention.
Figure 4B:
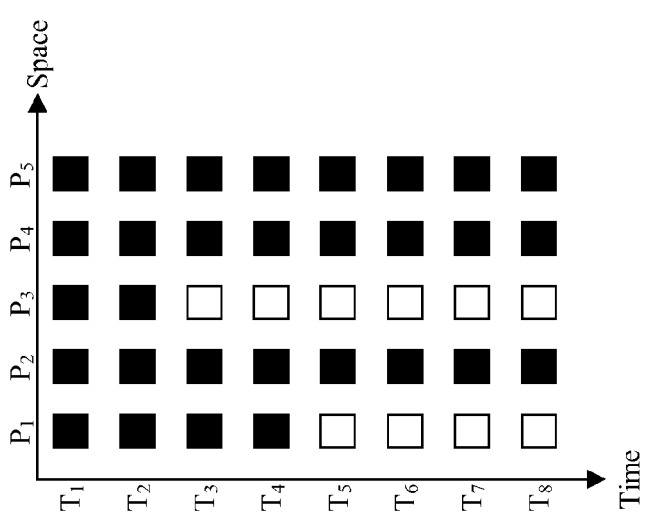
Figure 4A:
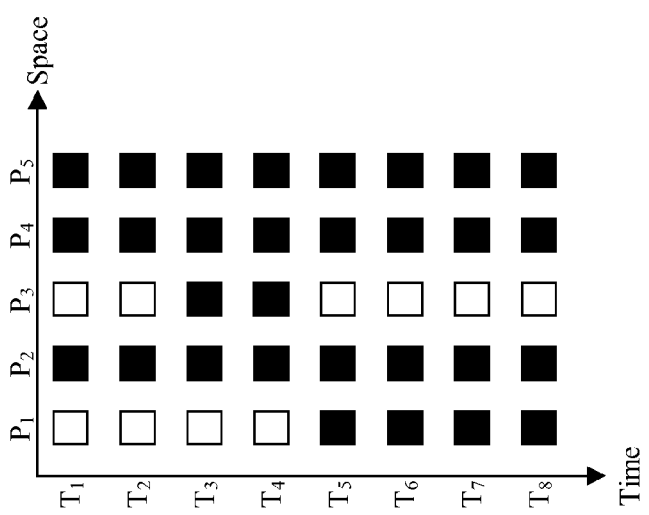

For example, the application of the (modified) cumulative difference algorithm to such an exemplary condition is represented schematically in FIGS. 4a-4c. Particularly, in FIG. 4a the same scenario of FIG. 2a is again repeated; however, the immobilized particle of contrast agent at the pixel $P_3$ now transiently disappears at the instants $T_3$-$T_4$ (with the pixel $P_3$ turning black and then returning white at the instant $T_5$). This may happen when a pixel (before applying the modified Min_IP algorithm for detecting the immobilized contrast agent) becomes black even for a single instant (since it is replaced by the minimum in the filtering set including this pixel value); therefore, after applying the modified Min_IP algorithm, the same pixel becomes black for a number of instants equal to the filtering length n of the modified Min_IP algorithm (2 in the example at issue).

In this condition, the application of the cumulative difference algorithm generates a corresponding image that is shown in FIG. 4b. As in the preceding case, the immobilized particle of contrast agents at the pixel $P_1$ (instants $T_1$-$T_4$) and at the pixel $P_3$ (instants $T_1$-$T_2$) disappear, while the detached particle of contrast agent at the pixel $P_1$ is detected and preserved (instants $T_5$-$T_8$). However, when the pixel $P_3$ turns black at the instant $T_3$ in FIG. 4a, it becomes white after applying the cumulative difference algorithm and then maintains this value; therefore, the transient disappearance of the immobilized particle of contrast agent at the pixel $P_3$ at the instant $T_3$ is interpreted as its detachment, even if the immobilized particle of contrast agent reappears immediately afterwards (instants $T_5$-$T_8$).

However, the above-mentioned problem may be solved by exploiting a comparison set of pixel values for calculating the variation (i.e., the decrease) of each pixel value (with respect now to the pixel value preceding this comparison set). The comparison set consists of the pixel value itself and the corresponding pixel values in one or more preceding images. More specifically, the cumulative difference algorithm is further modified according to the following formula (similar considerations apply if this modification is applied to the original cumulative difference algorithm):

$$OP(x,y,k)=OP(x,y,k-1)+\text{MAX}[0,IP(x,y,k-m)-CP(x,y,k)]$$

$$CP(x,y,k)=\text{MAX}[IP(x,y,k)\ldots IP(x,y,k-m+1)] \text{ with } m\geq 1,$$

where CP(x,y,k) is a comparison value used to determine the decrease of the pixel values; particularly, the comparison value CP(x,y,k) is defined as the maximum among the pixel values of the comparison set, which consists of the values of the same pixel in the image taken at the instant k and possibly in the preceding images taken from the instant k−1 back to the instant k−m+1. The number m specifies a comparison length indicating the number of pixel values in the comparison set (i.e., the number of images) that are taken into account for calculating the comparison value (down to a single pixel value as above when m=1). The comparison length m corresponds to a time window (given by the product of the comparison length m by the inverse of the imaging frame rate), which defines the degree of temporal low-pass filtering applied by the modified cumulative difference algorithm. Indeed, the modified cumulative difference algorithm now disregards any short decrease of the pixel values over time having a width smaller than the extent of the comparison window. In this way, the immobilized contrast agent will be considered detached only when it disappears from the relevant location for a time longer than the comparison window. Preferably, the value of the comparison length m (and then of the comparison window) is selected according to the quality of the available images (for example, ranging from 2 to 4-6). Particularly, higher values of the comparison length m allow removing the effects of noise and/or misalignment in images of very poor quality; however, this delays the instant at which the detached contrast agent is detected (since the corresponding pixel becomes white only after the pixel remained black for a period of time longer than the comparison window).

The application of the modified cumulative difference algorithm (with a comparison length m=3) to the same scenario of FIG. 4a generates a corresponding image that is shown in FIG. 4c. As can be seen, the pixels $P_2$, $P_4$-$P_5$ remain always black (instants $T_1$-$T_8$), since their values are stationary; the pixel $P_1$ becomes white at the instant $T_7$—with a delay of m−1 instants—and then remains so (since its value decreases). However, in this case the pixel $P_3$ is always black, since it does not decrease in two (or more) consecutive images. Therefore, any transient disappearing of the immobilized contrast agent (for a period of time at most equal to the comparison window) is filtered out.

This improves the robustness of the method; therefore, the detached contrast agent can be detected with a higher accuracy (thereby increasing the reliability of the obtained results).

Naturally, in a real application each pixel can be represented by any gray-scale level (instead of just black or white). Particularly, the pixel values are a function of the concentration of the immobilized contrast agent at the corresponding location; the pixels may be quite dark in the presence of a low concentration of the immobilized contrast agent (such as when a few particles thereof are immobilized) while they may be very bright in the presence of a high concentration of the immobilized contrast agent.

Figure 5B:
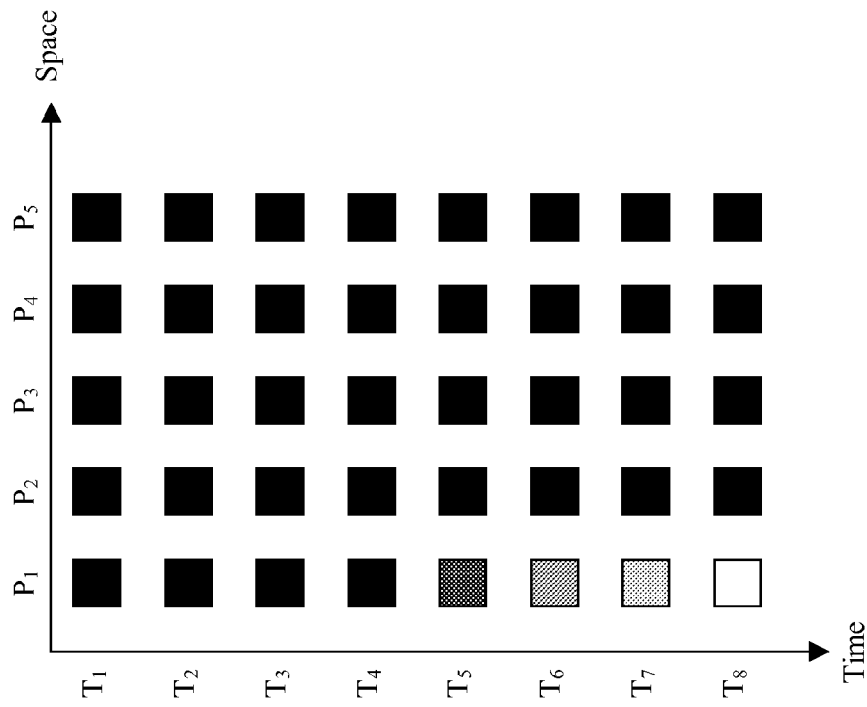
FIGS. 5a-5b are a schematic representation of another exemplary application of the solution according to an embodiment of the invention.
Figure 5A:
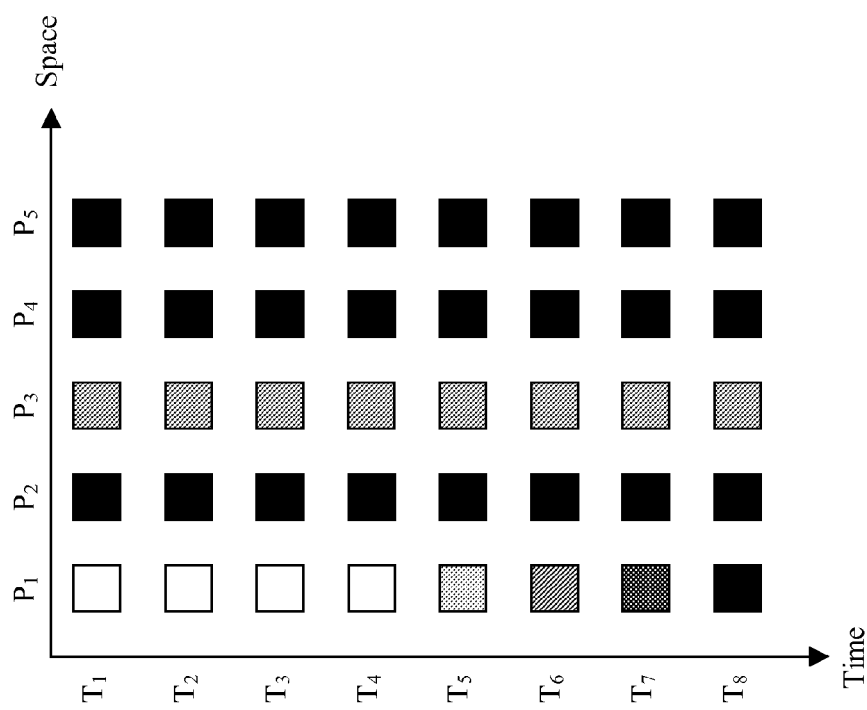

For example, the application of the (modified) cumulative difference algorithm to such an exemplary condition is represented schematically in FIGS. 5a-5b. Particularly, as shown in FIG. 5a, during instants $T_1$-$T_4$ many particles of contrast agent are immobilized at the pixel $P_1$ (white). Some of the immobilized particles of contrast agent at the pixel $P_1$ detach at the instant $T_5$, as shown by the pixel $P_1$ that darkens slightly (becoming light gray); the detachment of the immobilized particles of contrast agent at the pixel $P_1$ continues at the next instants $T_6$ (dark gray) and $T_7$ (far dark gray), until the instant $T_8$ when all the immobilized particles of contrast agent have left the pixel $P_1$ (completely black). At the same time, a few particles of contrast agent are immobilized at the pixel $P_3$ (gray) at the instants $T_1$-$T_8$.

The application of the cumulative difference algorithm (with a comparison length m=1) to this example generates the image shown in FIG. 5b. As in the preceding case, the immobilized particles of contrast agents at the pixel $P_3$ (instants $T_1$-$T_8$) disappear. As far as the immobilized particles of contrast agent detach from the pixel $P_1$, this pixel becomes dark gray (instant $T_5$), less dark gray (instant $T_6$), light gray (instant $T_7$), and finally white (instant $T_8$)—then maintaining this value.

Therefore, the cumulative difference algorithm also detects the gradual detachment of the target-specific contrast agent (when the pixel values become increasingly darker). At the same time, this provides additional information about the dynamic of the process (i.e., the rate of the detachment). Moreover, the pixel values so obtained allow quantifying the amount of the target-specific contrast agent that detaches (since the pixel values are proportional to the target-specific contrast agent concentration).

Similar considerations apply to the slowly-moving contrast agent. For example, the application of the cumulative difference algorithm to such an exemplary condition is represented schematically in FIGS. 6a-6c.

Figure 6C:
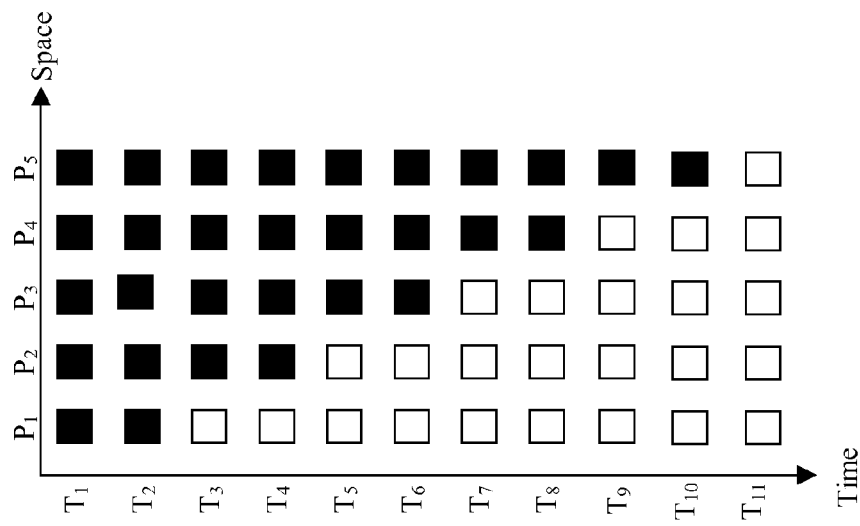
FIGS. 6a-6c are a schematic representation of a further exemplary application of the solution according to an embodiment of the invention.
Figure 6B:
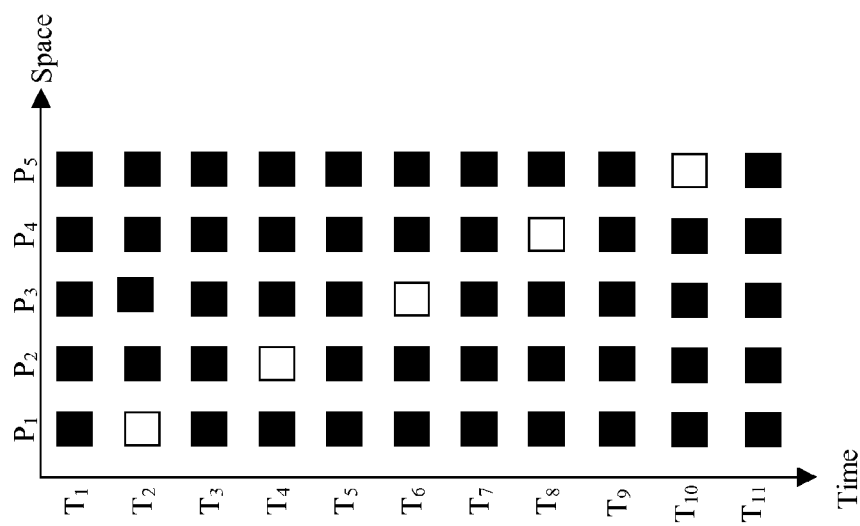
Figure 6A:
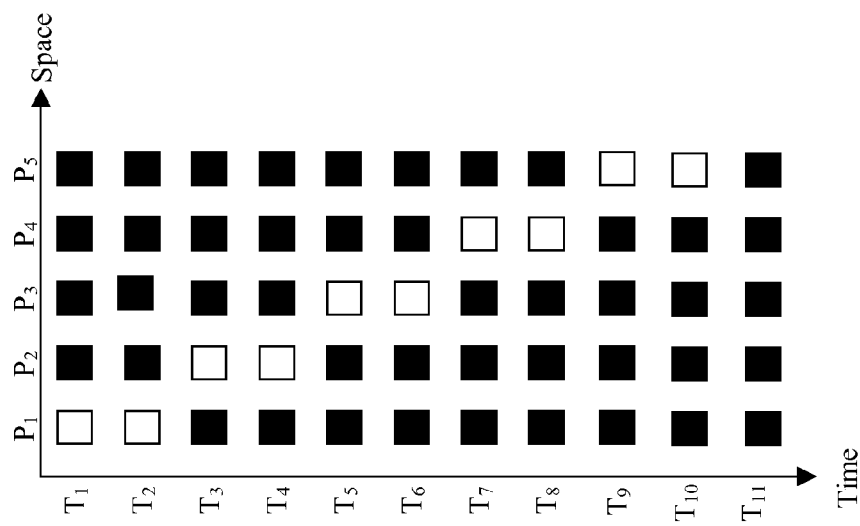

Particularly, FIG. 6a shows a sequence of images as original acquired (i.e., before applying the modified Min_IP algorithm to remove the contribution of the circulating contrast agent). In the example at issue, a slowly-moving particle of contrast agent reaches the pixel $P_1$ at the instants $T_1$; the slowly-moving particle of contrast agent remains at the same location at the next instant $T_2$. The slowly-moving particle of contrast agent then moves to the pixel $P_2$ (instants $T_3$-$T_4$), to the pixel $P_3$ (instants $T_5$-$T_6$), to the pixel $P_4$ (instants $T_7$-$T_8$), and to the pixel $P_5$ (instants $T_9$-$T_{10}$)—then exiting from the portion of the images shown in the figure (instant $T_{11}$).

The application of the modified Min_IP algorithm (with a filtering length n=2) to the example described above generates a corresponding image that is shown in FIG. 6b. As can be seen, every pixel $P_1$-$P_5$ is white only when it maintains this value for at least two consecutive instants; in the example at issue, this happens for the pixel $P_1$ at the instant $T_2$, the pixel $P_2$ at the instant $T_4$, the pixel $P_3$ at the instant $T_6$, the pixel $P_4$ at the instant $T_8$, and the pixel $P_5$ at the instant $T_{10}$. In this way, the slowly-moving particle of contrast agent is detected as soon as it remains stationary for a time at most equal to the duration of the filtering window of the modified Min_IP algorithm.

The application of the cumulative difference algorithm (with a comparison length m=1) to this example generates the image shown in FIG. 6c. As above, as soon each pixel $P_1$-$P_5$ turns from white to black between consecutive images it becomes white and then maintains this value; in the example at issue, this happens for the pixel $P_1$ (instants $T_3$-$T_{11}$), the pixel $P_2$ (instants $T_5$-$T_{11}$), the pixel $P_3$ (instants $T_7$-$T_{11}$), the pixel $P_4$ (instants $T_9$-$T_{11}$), and the pixel $P_5$ (instant $T_{11}$). As a result, whenever the slowly-moving particle of contrast agent leaves a pixel (where it was stationary for a period of time longer than the filtering window), the event is detected and preserved.

In a different embodiment of the present invention, it is possible to combine the modified Min_IP algorithm and the cumulative difference algorithm into a single formula. More formally, each pixel value is set to:

$$OP(x,y,k)=OP(x,y,k-1)+MAX[0,RP(x,y,k)-CP(x,y,k)]$$

$$CP(x,y,k)=MAX[IP(x,y,k)\ldots IP(x,y,k-+1)] \text{ with } m\geq 1,$$

$$RP(x,y,k)=MIN[IP(x,y,k-m)\ldots IP(x,y,k-m-n)] \text{ with } n\geq 1,$$

where RP(x,y,k) is a reference value used to determine the decrease of the pixel values; the reference value RP(x,y,k) is defined as above as the minimum among the pixel values of a reference set, which consists of the pixel values in the images preceding the comparison set from the instant k−m back to the instant k−m−n (and then with a number of pixel values equal to the filtering length n).

In this way, the desired result may be achieved with a single processing step (without having to remove the contribution of the circulating contrast agent beforehand).

Figure 7:
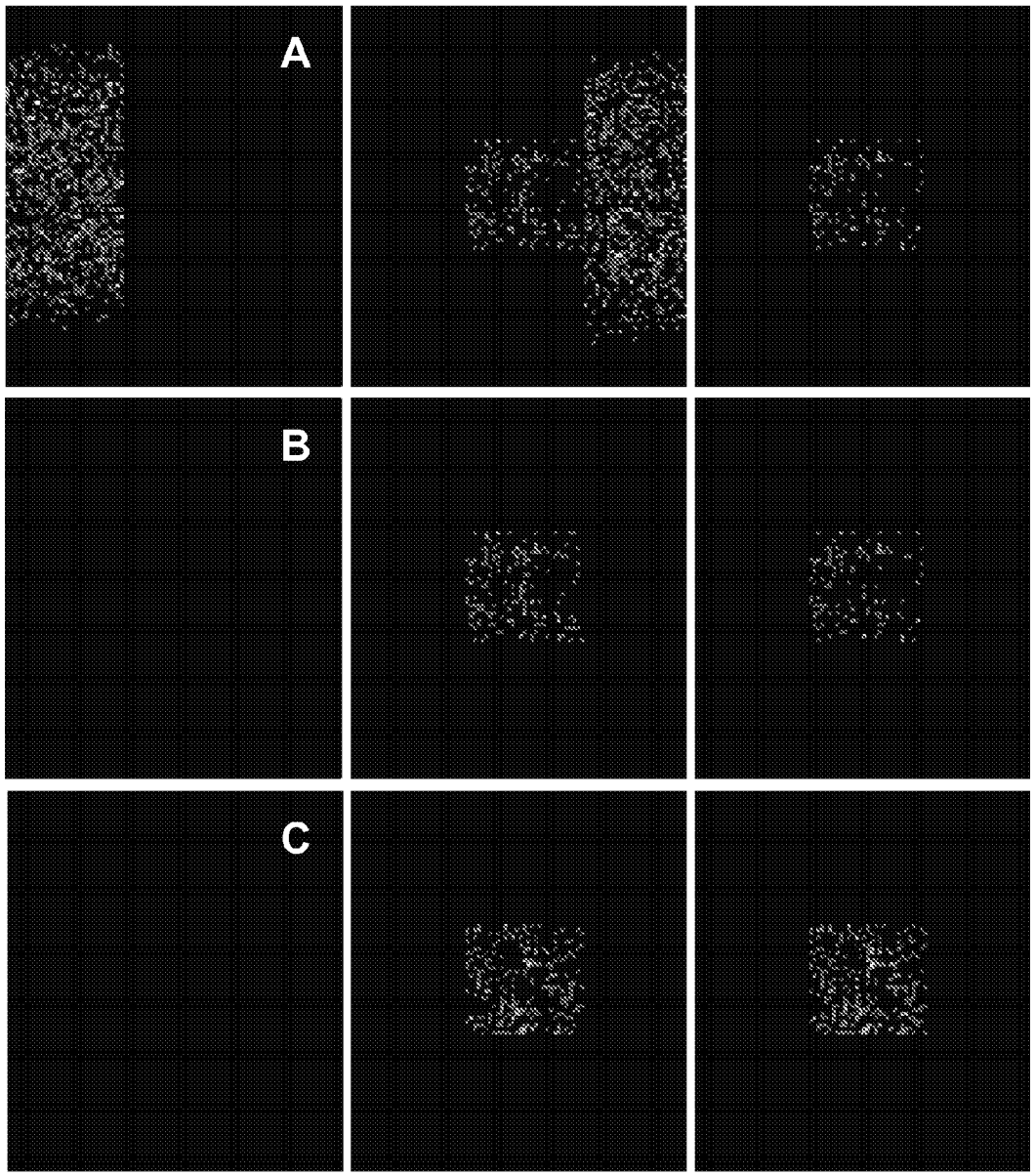
FIG. 7 shows an exemplary application of the solution according to an embodiment of the invention in a simulated situation.

The simulation of an exemplary application of the cumulative difference algorithm described above is illustrated in FIG. 7. Particularly, the figure shows the results that are obtained on a synthetic dataset simulating different instants of the passage of a volume of target-specific contrast agent (consisting of gas-filled microvesicles) over a target region (located in the center of the images). The leftmost column illustrates the situation before the target-specific contrast agent has reached the target region (wash-in phase), the middle column illustrates the situation when the target-specific contrast agent has just passed the target region (wash-out phase), and the rightmost column illustrates the situation at a late instant after the administration of the target-specific contrast agent (late phase) when all the circulating contrast agent has completely disappeared (e.g., due to lung filtration).

Row (A) represents the original sequence of (video) images. As may be seen, the immobilized contrast agent (in the target region) may be differentiated from the circulating contrast agent (and then detected) only after all the circulating contrast agent has left the target region. In the case the target-specific contrast agent is administered through a bolus injection, this may take several minutes; for the target-specific contrast agent administered through an infusion, the wash-out phase starts only after the infusion has been stopped (typically, after 10 minutes).

Row (B) represents the result obtained after the application of the modified Min_IP algorithm (using a filtering length n=9). As may be seen, the contribution of the circulating contrast agent is completely suppressed during the wash-in and wash-out phases; therefore, it is possible to detect the immobilized contrast agent as soon as it remains immobilized in the target region. However, the contrast agent that detaches from the target region disappears.

Row (C) represents the result obtained with the cumulative difference algorithm as described above (using a comparison length m=1). As may be seen, the contribution of the detached contrast agent is now detected; therefore, it is possible to locate the temporarily-immobilized contrast agent and/or the apparently-immobilized contrast agent as soon as it leaves the target region.

FIGS. 8a-8d show an example of in-vivo application of the above described algorithms. For this purpose, a region of inflamed tissue was induced by a 30 ml injection of TNF-α in the hind limb of a recombinant OF1 mouse, 6-10 weeks of age (TNF-α is a physiological proinflammatory cytokines secreted by macrophages and other cell-types and induces gene expression of P-Selectin). Gas-filled microvesicles were functionalized with a rat anti mouse P-Selectin antibody (CD62P, RB40.34, BD Pharmingen). The hind limb was analyzed by means of an imaging probe of the linear array type (15L8) connected to a Sequoia ultrasound scanner (Siemens Medical Solution, Erlangen, Germany). The ultrasound scanner was operated in CPS mode. The transmit frequency and mechanical index used were 14 MHz and 0.20, respectively. Randomized boluses of $7 \times 10^7$ bubbles of either target-specific contrast agent (i.e. the functionalized gas-filled microvesicles) or control contrast agent (i.e. the same gas-filled microvesicles, without the antibody) were administered in the jugular vein by a bolus injection at an initial instant t=0 minutes (in the same animal during successive experiments). The inflammation region was scanned for a period of 10 minutes, including the wash-in and wash-out phases of the contrast agent. The images so obtained were recorded on tape using a digital video recorder and processed off-line in a region of interest, which included part of the hind limb containing the inflamed tissue; the results obtained by applying the above-described algorithms were superimposed on the original images.

Figure 8A:
FIGS. 8a-8d show an example of in-vivo application of the solution according to an embodiment of the invention.
Figure 8B:
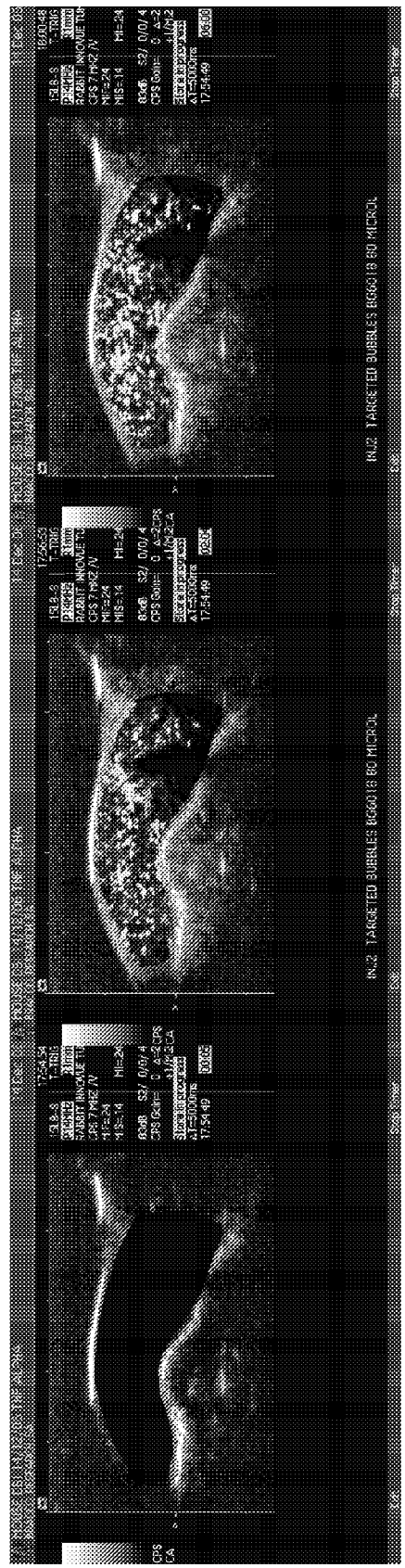

The images were first pre-processed to reduce the contribution of the circulating contrast agent (by means of the modified Min_IP algorithm with a filtering length n=12 applied in the region of interest); the corresponding images are shown in FIG. 8a and in FIG. 8b for the control contrast agent and the target-specific contrast agent, respectively. The images on the left-hand side relate to the instant immediately after the injection of the contrast agent. As may be seen, the region of interest in the images is completely black, since the contrast agent has not reached yet the corresponding region of the body-part. The images in the middle depict the situation 2 minutes after the injection of the contrast agent (at the beginning of the wash-out phase). The depiction of the control contrast agent shown in FIG. 8a is due to the relatively high concentration of the contrast agent (the Min_IP algorithm is unable to suppress the high concentration of circulating contrast agent with a window length of n=12 in the bigger arteries). It is clear from FIG. 8b that a high fraction of particles of the target-specific contrast agent are depicted to be attached to the inflamed tissue (target tissue) by the Min_IP algorithm. A homogeneous opacification of the whole region of inflamed tissue is shown. This is even more evident in the images shown on the right-hand side, which depict the situation 6 minutes after the injection of the contrast agent. The control contrast agent is hardly visible (FIG. 8a), whereas the target-specific contrast agent (FIG. 8b) nicely delineates the region of inflamed tissue.

Figure 8C:
Figure 8D:
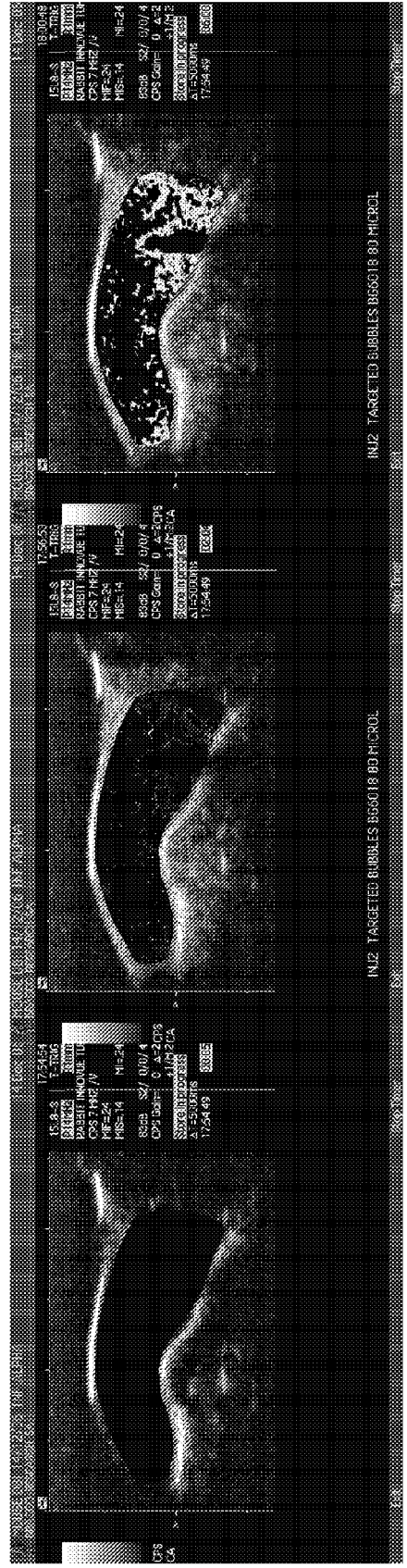

FIGS. 8c-8d show the situation after the application of the cumulative difference algorithm (with a comparison length m=2), for the control contrast agent and the target-specific contrast agent, respectively. The images shown on the left-hand side, in the middle and on the right-hand side in these figures, correspond to the same instants as mentioned above (i.e., immediately after injection, 2 minutes after injection and 6 minutes after injection of the contrast agent, respectively). It is clear from the images on the right-hand side of FIG. 8c, that most of the particles of the control contrast agent are detached 6 minutes after injection, indicating the high non-specificity of the control contrast agent. However, at the same instant, only a few particles of the target-specific contrast agent are detached (right-hand side of FIG. 8d), showing its high specificity. Moreover, the locations of the detached particles are nicely spatially depicted, possibly indicating regions of lower binding strength (due to a lower receptor density), or regions of non-specific binding (due to the absence of the specific receptors).

Figure 9:
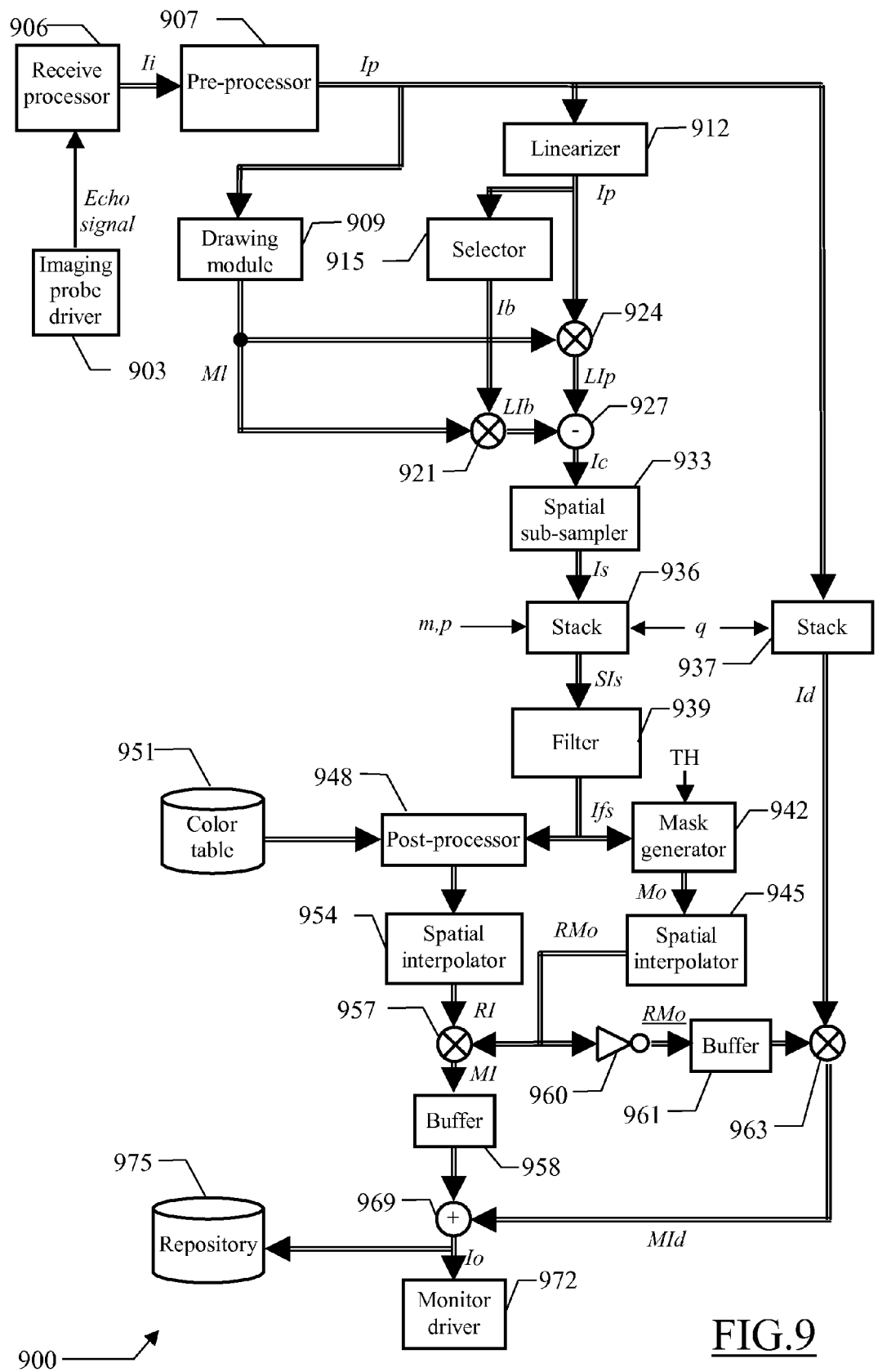
FIG. 9 depicts the main software and hardware components that can be used for practicing the solution according to an embodiment of the invention.

Moving now to FIG. 9, the main software and hardware components that can be used for practicing the solution according to an embodiment of the invention are denoted as a whole with the reference 900. The information (programs and data) is typically stored on the hard disk and loaded (at least partially) into the working memory when the programs are running, together with an operating system and other application programs (not shown in the figure). The programs are initially installed onto the hard disk, for example, from CD-ROM.

Particularly, a driver 903 controls the imaging probe (not shown in the figure); for example, the imaging probe driver 903 includes a transmit beam former and pulsers for generating the ultrasound pulses to be applied to the body-part under analysis. The corresponding (analog RF) echo signal that is received from said body-part is supplied to a receive processor 906. Typically, the receive processor 906 pre-amplifies the analog RF echo signal and applies a preliminary time-gain compensation (TGC); the analog RF echo signal is then converted into digital values by an Analog-to-Digital Converter (ADC), and combined into a focused beam signal through a receive beam former. The digital signal so obtained may be processed through further digital algorithms and other linear or non-linear signal conditioners (such as a post-beam-forming TGC). Particularly, the receive processor 906 applies a contrast-specific algorithm to suppress the contribution of tissue (such as based on the above-mentioned HI, PI, PM or CPS techniques). The digital signal is then demodulated, log-compressed, and scan-converted into a video format. This process results in the recording of a sequence of (video) input images Ii (each one including M×N pixel values). More specifically, each pixel value of the input images Ii is determined by the intensity of the acoustical response at the location in the body-part corresponding to said pixel.

Optionally, the receive processor 906 includes a motion compensation module, carrying out a method for reducing the misalignment of the input images Ii with respect to a reference image (for example, due to motion resulting from patient breathing or from involuntary movement of the imaging probe); an example of motion compensation method that is well suited for this purpose is described in WO-A-2006/015971, the entire disclosure of which is herein incorporated by reference.

The input images Ii are supplied to a pre-processor 907. The pre-processor 907 removes the contribution of the circulating contrast agent in the input images Ii. The pre-processor 907 may apply the method described in the above-mentioned International patent application No. PCT/EP2006/068305. In this way, each input image Ii is converted into a corresponding pre-processed image Ip; the pre-processed image Ip provides a representation of the (permanently-, temporarily- and apparently-) immobilized contrast agent in a region of interest, which information may be overlaid on the original input images Ii.

A drawing module 909 is used to predefine a region-of-interest for the analysis of the pre-processed images Ip (typically the same as the one used by the pre-processor 907). The operation generates a limitation mask Ml, which consists of a matrix of binary values with the same size as the pre-processed images Ip (i.e., M×N); all binary values inside the region of interest are assigned the logic value 1, whereas the binary values outside the region of interest are assigned the logic value 0.

A linearizer 912 is optionally used to linearize the pre-processed images Ip, so as to make each pixel value thereof directly proportional to the corresponding local concentration of the immobilized contrast agent; for example, this result may be achieved by applying an inverse log-compression and then squaring the value so obtained (for example, as described in WO-A-2004/110279, the entire disclosures of which is herein incorporated by reference).

A selector 915 is used to select and latch one of the (video or linearized) pre-processed images Ip to be used as a background image (denoted with Ib); for example, the background image Ib is selected among the pre-processed images Ip taken before the contrast agent has reached the body-part under analysis.

A multiplier operator 921 receives the background image Ib (from the selector 915) and the limitation mask Ml (from the drawing module 909). The operator 921 multiplies the background image Ib by the limitation mask Ml pixel-by-pixel, so as to generate a corresponding limited background image LIb (this operation needs to be done only once, but it may be repeated any time during the analysis process). Another multiplier operator 924 receives the pre-processed images Ip in succession (from the linearizer 912) and the limitation mask Ml (from the drawing module 909). The operator 924 multiplies each pre-processed image Ip by the limitation mask Ml pixel-by-pixel, so as to generate a corresponding sequence of limited pre-processed images LIp. As a result, the limited background image LIb and the limited pre-processed images LIp only include the pixel values of the background image Ib and of the pre-processed images Ip, respectively, that are inside the region of interest (defined by the limitation mask Ml), while the other pixel values are reset to 0.

A difference operator 927 receives the limited background image LIb (from the multiplier 921) and the limited pre-processed images LIp (from the multiplier 924). The operator 927 subtracts the limited background image LIb from each limited pre-processed images LIp pixel-by-pixel, so as to remove any residual clutter (for example, due the contribution of tissue that has not been completely removed by the contrast-specific algorithm applied by the receive processor 906). The operation generates a corresponding sequence of corrected images Ic, which is provided to a spatial sub-sampler 933.

The module 933 sub-samples the corrected images Ic according to a factor determined by the spatial resolution of the corrected images Ic along each dimension (for example, 2 to 6 pixels). The spatial sub-sampling may comprise low-pass filtering followed by sub-sampling according to a sub-sampling factor. The low-pass filtering has a cutoff frequency, which may be chosen as the highest frequency component containing significant energy in a selected one of the corrected images Ic (for example, determined by Fourier analysis). The sub-sampling is performed according to a factor that may be determined, for example, as a value resulting in a spatial sub-sampling frequency equal to twice the cutoff frequency. In this way, each corrected image Ic is transformed into a corresponding (spatially) sub-sampled image Is; each value of the sub-sampled image Is thus represents a cell corresponding to a group of adjacent pixels in the correct image Ic (which cell has a size defined according to the above-mentioned spatial resolution).

The sub-sampled images Is so obtained are stored in succession into a stack 936, which acts as a buffer memory for further processing according to the above-described cumulative difference algorithm. The stack 936 provides storage for q sub-sampled images Is. The value of q is determined by the choice of the comparison depth m of the cumulative difference algorithm and a temporal sub-sampling parameter p (ranging from 0 to m−2), according to the relation $q=(m+1)(p+1)$. The required set of m+1 sub-sampled images SIs among the ones available in the stack 936 (for the reference set of m sub-sampled image Is and the preceding sub-sampled image Is) is thus created and made available for further processing. In most practical situations, the sub-sampling parameter p is set to 0 so that $q=m+1$. The set of sub-sampled images SIs then consists of the last m+1 sub-sampled images Is stored in the stack 936 (so that every sub-sampled image Is is considered). Conversely, when the sub-sampling parameter p is higher than 0, q sub-sampled images Is (q>m+1) must be stored in the stack 936, in order to make m+1 sub-sampled images Is available for the application of the cumulative difference algorithm. This temporal sub-sampling may be advantageously exploited when the ultrasound scanner works at ultra-high frame rates (for example, 100-500 images per second), in which case an analysis of every available sub-sampled image Is does not provide any useful benefit.

At the same time, the (original) pre-processed images Ip provided by the pre-processor 907 are latched into another stack 937, which consists of a first-in-first-out (FIFO) shift register, with a size equal to q (so as to store the last q pre-processed images Ip).

A filter 939 receives the set of (m+1) sub-sampled images SIs from the stack 936. The filter 939 calculates a filtered image Ifs by applying the above-described cumulative difference algorithm on this set of sub-sampled images SIs.

The filtered image Ifs so obtained is then passed to a mask generator 942, which also receives a predefined threshold value TH for the cell values (for example, ranging from 0 to 5% of their maximum allowable value). The mask generator 942 creates a corresponding overlay mask Mo; the overlay mask Mo is obtained from the filtered image Ifs by assigning (to each cell) the logic value 1 if its value is strictly higher than the threshold value TH or the logic value 0 otherwise.

The overlay mask Mo is subsequently provided to a spatial-interpolator 945. The spatial-interpolator 945 restores the full-size of the overlay mask Mo corresponding to the size of the input images Ii (i.e., M×N binary values); for this purpose, the value of each cell in the overlay mask Mo is replicated for the corresponding group of pixels. The operation generates a corresponding interpolated mask RMo.

At the same time, the filtered image Ifs is also provided to a post-processor 948. The post-processor 948 optionally converts the cell values of the filtered image Ifs into corresponding discrete values (for example, consisting of 64 or 128 levels that are uniformly distributed between the lowest value and the highest value of all the cells), by possibly applying a gain factor. Optionally, when the input images Ii are linearized by the module 912, the post-processor 948 may also apply a non-linear processing (such as a log-compression) so as to produce images with well-balanced contrast. The post-processor 948 also accesses a color lookup table 951. The color lookup table 951 associates all the possible levels with the representation of corresponding colors (that are preferably brighter as the levels increase); for example, each color is defined by an index for accessing a location within a palette containing its actual specification. In this way, each cell in the filtered image Ifs is assigned the corresponding color representation.

The filtered image Ifs (either post-processed or as originally built) is provided to another spatial-interpolator 954. The spatial-interpolator 954 restores the full-size of the filtered image Ifs corresponding to the size of the input images Ii (i.e., M×N pixel values) by means of interpolation techniques (such as based on the nearest neighbor, bilinear, or bicubic technique). For this purpose, the value of each cell in the filtered image Ifs is replicated for the corresponding group of pixels (nearest neighbor interpolation method) and optionally filtered spatially (such as using a low-pass 2D or 3D spatial filter). The operation generates a corresponding interpolated image RI.

A multiplier operator 957 receives the interpolated image RI (from the spatial interpolator 954) and the interpolated mask RMo (from the spatial interpolator 945). The operator 957 multiplies the interpolated image RI with the interpolated mask RMo pixel-by-pixel, so as to obtain a masked image MI; as a result, the masked image MI only includes the pixel values of the corresponding interpolated image RI that are higher than the threshold value TH (while the other pixel values are reset to 0). The threshold value TH allows tuning the level of masking of the interpolated image RI, down to none when TH=0; indeed, in this case every pixel of the overlay mask Mo and of the interpolated overlay mask RMo is at the logic value 1, so that the masked image MI will be exactly the same as the interpolated image RI. The masked image MI is then latched into a single-image buffer 958 (replacing its previous content). In this way, the masked image MI in the buffer 958 is updated whenever the filter 939 outputs a new filtered image Ifs, while it remains unchanged otherwise (so as to maintain the masked image MI that was obtained from the filtered image Ifs last calculated).

The interpolated mask RMo is also supplied from the spatial interpolator 945 to an inverter 960, which generates a corresponding inverted interpolated mask RMo (by exchanging the logic values 0 and 1). The interpolated mask RMo is likewise latched into another single-image buffer 961 (replacing its previous content), so as to be always synchronized with the masked image MI in the buffer 958. The inverted interpolated mask RMo latched in the buffer 961 is then passed to a multiplier operator 963. The multiplier operator 963 also receives a delayed image Id from the stack 937. Every time the inverted interpolated mask RMo is latched into the buffer 961, the corresponding delayed image Id exits from the stack 937, thus allowing the operator 963 to multiply the delayed image Id and the inverted interpolated mask RMo, pixel-by-pixel, so as to obtain a masked delayed image MId; as a result, the masked delayed image MId only includes the pixel values of the delayed image Id that are not included in the corresponding masked image MI (while the other pixel values are reset to 0).

An adder operator 969 receives the masked delayed image MId (from the multiplier 963) and the masked image MI (latched in the buffer 958). The operator 969 adds the masked image MI and the masked delayed image MId pixel-by-pixel (correctly synchronized) so as to obtain an overlay image Io. In this way, each pixel value of the delayed image Id is overridden by the corresponding pixel value of the masked image MI if and only if the latter has a significant value (i.e., higher than the threshold value TH).

The overlay image Io is passed to a monitor driver 972, which controls its visualization. At the same time, the overlay image Io may also be added to a repository 975. The same operations described above are reiterated for each new input image it that is recorded. Particularly, the corresponding pre-processed image Ip is pushed into the stack 937; this causes the shifting of the preceding pre-processed images Ip in the stack 937, and the output of the oldest one. At the same time (after optional linearization, limitation to the desired region of interest, subtraction of the background image Ib, and spatial sub-sampling) the corresponding sub-sampled image Is is added to the stack 936. As a result, the overlay images Io are displayed in succession on the monitor of the ultrasound scanner; it should be noted that each overlay image Io is available with a delay (with respect to the acquisition time of the corresponding input image Ii), which is defined by the time required to apply the modified Min_IP algorithm (in the pre-processor 907) plus the time required to apply the cumulative difference algorithm (i.e., to cross the whole stack 937). Moreover, the sequence of overlay images Io so obtained is also available in the repository 975 for further analysis.

In this way, the detached contrast agent is easily recognized (by its color coding) with respect to the permanently-immobilized contrast agent and the possible background (in the original gray-scale pixel levels)—with the degree of overlay that may be updated according to contingent requirements (by means of the threshold value TH), so as to tune the impact of the operation on the pre-processed images Ip. The reading of the overlay images Io is further facilitated when each different color (representing the concentration of the immobilized contrast agent that has detached) bears a quantitative meaning of its own; for example, this value can be read out from a color bar, which is displayed on the monitor close to the sequence of overlay images Io. Moreover, when the pre-processed images Ip show the immobilized contrast agent over the original input images Ii, the overlay images Io provide an enhanced visual perception of the detached contrast agent, which is contextualized on the actual representation of the body-part under analysis.

In any case, the proposed solution facilitates the spatial delineation and the quantification of the permanently-immobilized contrast agent, the temporarily-immobilized contrast agent, and/or the apparently-immobilized contrast agent, thereby allowing the correct detection of the pathologies of interest. Therefore, the accuracy of any analysis of the obtained results is strongly increased.

MODIFICATIONS

Naturally, in order to satisfy local and specific requirements, a person skilled in the art may apply to the solution described above many modifications and alterations. More specifically, although one or more embodiments of the present invention have been described with a certain degree of particularity, it should be understood that various omissions, substitutions and changes in the form and details as well as other embodiments are possible. Particularly, an embodiment may even be practiced without the specific details (such as the numerical examples) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any disclosed embodiment of the invention may be incorporated in any other embodiment as a matter of general design choice.

For example, an embodiment lends itself to be implemented with an equivalent method (by using similar steps, removing some steps being non-essential, or adding further optional steps); moreover, the steps may be performed in a different order, concurrently or in an interleaved way (at least in part).

According to an alternative embodiment, the pixel values outside the selected region of interest may be reset to 0 (so that the portion of the overlay image outside the region of interest is black); however, the application of an embodiment to the whole content of the images is contemplated (without selecting any region of interest).

It is emphasized that the above-described applications of the disclosed embodiments are merely illustrative, and they must not be interpreted in a limitative manner. For example, it is possible to administer a target-specific contrast agent in its basic formulation without the relevant ligand; the detection of any detached contrast agent allows identifying undesired interactions of the target-specific contrast agent with other passive targets.

Likewise, an embodiment of the invention lends itself to be put into practice with equivalent target-specific contrast agents for whatever (biological) target; for example, the contrast agent may be specific for enhancing Magnetic Resonance imaging or X-ray Computed Tomography imaging. However, the application of the same solution to a non target-specific contrast agent—for example, for detecting the slowly-moving contrast agent only—or even to a mixture of target-specific contrast agent and non target-specific contrast agent, is not excluded.

As described in detail above, an embodiment of the present invention may be put into practice by starting from images wherein the contribution of the circulating contrast agent has already been removed (or at least substantially reduced); this result may be achieved by applying the modified Min-IP algorithm. However, it is also possible to wait until the circulating contrast agent has disappeared, or to apply any other algorithm providing equivalent outcomes. Alternatively, the same result may also be achieved by acting directly on the original images (i.e., removing the circulating contrast agent and the temporarily/apparently-immobilized contrast agent at the same time). Anyway, an embodiment according to the present invention also lends itself to be implemented with whatever algorithm, which is capable of detecting the contrast agent leaving any location after being substantially immobilized thereon (for a period of time longer that a pre-defined duration). For example, in a very simplified implementation it is possible to compare the images taken during the analysis process (with the permanently-, temporarily- and apparently-immobilized contrast agent) with an image taken at the end of the analysis process (wherein the temporarily/apparently-immobilized contrast agent disappeared to leave the permanently-immobilized contrast agent only).

Although an embodiment of the proposed technique may find application for monitoring the evolution of the body-part over time during the analysis process, nothing prevents providing a single image at a specific instant (for example, at the end of the wash-in phase). In any case, each filtered value may be calculated by accumulating the preceding variation values in a different way; for example, it may be possible to avoid processing the pixels once they have become white, or to calculate the filtered values directly according to the history of the corresponding pixel values.

Although an embodiment of the present invention has been specifically designed for use in real-time, the analysis of the obtained results off-line is within the scope of the invention.

Moreover, the proposed cumulative difference algorithm may be implemented by setting the comparison value to either the current pixel value or a comparison value based on a comparison set of pixel values at multiple instants; in the latter case, the set may have any other size, even defined dynamically according to an estimated quality of the available images.

Alternatively, the temporal sub-sampling of the input images may be performed according to any other criteria (or it may be omitted altogether).

The use of different formulas for setting the comparison value (based on the corresponding set of pixel values) is contemplated.

An embodiment of the solutions described above assumes a direct relation between the amplitude of the echo signal and the corresponding pixel value (i.e., a larger amplitude of the echo signal results in a brighter pixel). Conversely, in a system based on negative images (wherein the pixel values decrease with the amplitude of the echo signal) all the equations given above would need to be modified to reflect the reverse logic.

Likewise, any other formula may be used to calculate the variation value to be accumulated (so as to indicate the variation of the comparison value with respect to the reference value, consisting of either the preceding pixel value or a value based on a reference set of multiple preceding pixel values). More generally, the filtered images may be generated by any other algorithm capable of detecting the different persistence of the contrast agent at each location (as defined by the time pattern of the corresponding pixel values).

Moreover, any other technique for acquiring the input images is within the scope of the present invention (for example, using Doppler-based algorithms). Alternatively, the original images used as background in the overlay may also be based on non contrast-specific images (such as fundamental B-mode images being obtained from the echo signals of the imaging probe driver). Naturally, an embodiment of the proposed method may still be applied on images provided by a contrast-specific imaging modality for generating the filtered images.

It should be appreciated that the feature relating to the subtraction of the background image is not strictly necessary (and it may be omitted in some embodiments of the invention).

Similar considerations apply if the images are spatially sub-sampled with a different procedure (for example, according to a predefined sub-sampling factor), or if the spatial sub-sampling is performed beforehand or afterward; in any case, the application of an embodiment the proposed solution at the pixel level (instead of at the level of groups of pixels defined by the above-mentioned spatial sub-sampling) is not excluded.

Likewise, it is also possible to omit compensating the motion of the input images (for example, when this motion is far slower than the flow of the circulating contrast agent).

Alternatively, the images may be linearized in a different way; for example, the linearized images might be already available for other purposes (such as when parametric analysis techniques are implemented); in this case, it is possible to exploit the available information without any additional linearization operation. Anyway, nothing prevents the application of an embodiment of the proposed solution to the log-compressed images directly.

It may also be possible to leave the choice of overlaying the filtered images on the pre-processed images to the preference of a user; for example, the pixel values of the (original) pre-processed images within the region of interest may be set to zero in order to display the filtered images against a black background, thus improving contrast. More generally, the obtained information may be used in any other way. For example, it may be possible to display the filtered images alone, to overlay the filtered images on the input images (without the pre-processing to remove the contribution of the circulation contrast agent), to overlay the filtered images on the pre-processed images within the region of interest and on the input images outside the region of interest, and in any other combination thereof; moreover, it may be possible to subtract the filtered images from the pre-processed images to remove the contribution of the temporarily/apparently-immobilized contrast agent.

Alternatively, any other different visual coding may be used to differentiate the detached contrast agent from the permanently-immobilized contrast agent in the overlay images; for example, it may be possible to use shades of a first color (such as yellow) for the detached contrast agent, and shades of a second color (such as red) for the permanently-immobilized contrast agent (over a background in gray scale).

Similar considerations may apply if the program (which may be used to implement each embodiment of the invention) is structured in a different way, or if additional modules or functions are provided; likewise, the memory structures may be of other types, or may be replaced with equivalent entities (not necessarily consisting of physical storage media). In any case, the program may take any form suitable to be used by any data processing system or in connection therewith (for example, within a virtual machine); particularly, the program may be in the form of external or resident software, firmware, or microcode (either in object code or in source code—for example, to be compiled or interpreted). Moreover, it may be possible to provide the program on any computer-usable medium; the medium can be any element suitable to contain, store, communicate, propagate, or transfer the program. For example, the medium may be of the electronic, magnetic, optical, electromagnetic, infrared, or semiconductor type; examples of such medium are fixed disks (where the program can be pre-loaded), removable disks, tapes, cards, wires, fibers, wireless connections, networks, broadcast waves, and the like. In any case, an embodiment according to the present invention lends itself to be implemented with a hardware structure (for example, integrated in a chip of semiconductor material), or with a combination of software and hardware.

Similar considerations may apply if the ultrasound scanner has a different structure or includes other units (such as with an imaging probe of the linear-, convex-, phased-, or matrix-array type). Alternatively, an embodiment may be applied in a medical imaging system that consists of an ultrasound scanner and a distinct computer (or any equivalent data processing system); in this case, the measured data is transferred from the ultrasound scanner to the computer for its processing (for example, through a removable disk, a memory key, or a network connection). In any case, the application to any other medical imaging system, such as based on Magnetic Resonance Imaging (MRI) or X-ray Computed Tomography (CT), is within the scope of the invention.

Naturally, in order to satisfy local and specific requirements, a person skilled in the art may apply to the embodiments described above many modifications and alterations. Particularly, although one or more embodiments have been described with a certain degree of particularity, it should be understood that various omissions, substitutions, and changes in the form and details as well as other embodiments are possible. Moreover, it is expressly intended that specific elements and/or method steps described in connection with any disclosed embodiment may be incorporated in any other embodiment as a general matter of design choice.

The invention claimed is:

1. A method for imaging a body-part being perfused with a contrast agent, wherein the method includes the steps of:
providing a sequence of input images offering a digital representation over time of the body-part, each input image including a plurality of input values each one indicative of a response to an interrogation signal of a corresponding location of the body-part possibly including the contrast agent; and
generating at least one filtered image from a plurality of selected ones of the input images, wherein each filtered image includes a filtered value for each of a plurality of selected ones of the locations, the filtered value of each selected location being indicative of the contrast agent leaving the selected location after being substantially stationary at the selected location for a period of time comprised between a first non-zero threshold and a second threshold higher than the first threshold, the filtered value being obtained by:
reducing a contribution of the contrast agent being substantially stationary at the selected location along the selected input images for a period of time equal to or shorter than the first threshold; and
reducing a contribution of the contrast agent being substantially stationary at the selected location along the selected input images for a period of time equal to or longer than the second threshold.

2. The method according to claim 1, wherein the contrast agent is a target-specific contrast agent being capable of circulating within the patient and of being substantially immobilized on a biological target, each filtered value being indicative of the contrast agent detaching from the selected location after being temporarily immobilized at the selected location for a period of time comprised between the first threshold and the second threshold and/or moving slowly to remain at the selected location for a period of time comprised between the first threshold and the second threshold.

3. The method according to claim 1, wherein the step of providing the sequence of input images includes:
pre-processing the input images to reduce a contribution of the contrast agent being substantially stationary at each location along the selected input images for a period of time equal to or shorter than the first threshold,
and wherein the step of generating includes:
calculating each filtered value in each filtered image by cumulating a variation value indicative of a variation of a comparison value, said comparison value being based on a comparison set of input values for the selected location in a comparison set of the selected input images including a specific selected input image corresponding to the filtered image, with respect to a reference value, said reference value being equal to the input value for the selected location in one of the selected input images preceding the comparison set of selected input images in the sequence.

4. The method according to claim 1, wherein the step of generating includes:
calculating each filtered value in each filtered image by cumulating a variation value indicative of a variation of a comparison value, said comparison value being based on a comparison set of input values for the selected location in a comparison set of the selected input images including a specific selected input image corresponding to the filtered image, with respect to a reference value, said reference value being indicative of the lowest response of the selected location in a reference set of the selected input images preceding the comparison set of selected input images in the sequence.

5. The method according to claim 3, wherein the at least one filtered image consists of a further sequence of filtered images, the step of generating including:
   calculating the filtered value in each filtered image by cumulating the variation value with the filtered value in one of the filtered images preceding the filtered image in the further sequence.

6. The method according to claim 3, further including:
   displaying each filtered image substantially in real-time with an acquisition instant of the specific selected input image.

7. The method according to claim 3, wherein the comparison set of selected input images consists of the specific selected input image, the step of calculating each filtered value in each filtered image including:
   setting the comparison value to the input value for the selected location in the specific selected input image.

8. The method according to claim 3, wherein the comparison set of selected input images consists of the specific selected input image and at least one of the selected input images preceding the specific selected input image in the sequence.

9. The method according to claim 8, wherein the step of calculating each filtered value in each filtered image includes:
   temporally sub-sampling the comparison set of selected input images.

10. The method according to claim 8, wherein the step of calculating each filtered value in each filtered image includes:
    setting the comparison value to one of the input values of the comparison set of selected input values being indicative of the highest response of the selected location.

11. The method according to claim 10, wherein each input value increases with the response of the corresponding location, the step of calculating each filtered value in each filtered image including:
    setting the comparison value to the maximum of the comparison set of input values.

12. The method according to claim 3, wherein the step of calculating each filtered value in each filtered image includes:
    setting the variation value to an absolute value of a difference between the comparison value and the reference value.

13. The method according to claim 3, wherein the step of calculating each filtered value in each filtered image includes:
    setting the variation value to:
      a delta value indicative of a decrease of the response of the selected location from the reference value to the comparison value when the response of the selected location decreases from the reference value to the comparison value, or
      a null value otherwise.

14. The method according to claim 13, wherein each input value increases with the response of the corresponding location, the step of calculating each filtered value in each filtered image including:
    setting the variation value to:
      the reference value minus the comparison value when the comparison value is lower than the reference value, or
      zero otherwise.

15. The method according to claim 1, wherein the body-part includes a tissue, the step of providing the sequence of input images including:
    reducing a contribution of the tissue in the input images.

16. The method according to claim 1, wherein the step of generating includes:
    selecting a background image in the sequence of input images, and
    subtracting the background image from the selected input images.

17. The method according to claim 1, wherein the step of generating includes:
    spatially sub-sampling the selected input images according to an estimated resolution thereof.

18. The method according to claim 1, wherein the step of providing the sequence of input images includes:
    selecting a reference image in the sequence of input images and compensating a motion of each selected input image with respect to the reference image.

19. The method according to claim 1, wherein the step of generating includes:
    linearizing the selected input images to make each input value thereof substantially proportional to a concentration of the contrast agent at the corresponding location.

20. The method according to claim 1, wherein the step of generating includes:
    reducing each filtered image by resetting each filtered value in the filtered image not reaching a predefined threshold, and
    creating an overlay image by overlaying each input image with a corresponding one of the reduced filtered images.

21. The method according to claim 20, wherein the step of generating includes:
    representing, in each overlay image, each filtered value according to a first visual coding and each input value according to a second visual coding.

22. A computer program on a non-transitory storage medium configured for performing the method of claim 1 when the computer program is executed on a data processing system.

23. A medical imaging system including a computer program on a non-transitory storage medium configured to perform the steps of the method according to claim 1 when the computer program is executed on a data processing system.

* * * * *